US009516408B2

(12) United States Patent
Zakis

(10) Patent No.: US 9,516,408 B2
(45) Date of Patent: Dec. 6, 2016

(54) METHOD AND APPARATUS FOR WIND NOISE DETECTION

(71) Applicant: Cirrus Logic International Semiconductor Limited, Edinburgh (GB)

(72) Inventor: Justin Andrew Zakis, Richmond (AU)

(73) Assignee: Cirrus Logic International Semiconductor Limited, Edinburgh (GB)

( * ) Notice: Subject to any disclaimer, the term of this patent is extended or adjusted under 35 U.S.C. 154(b) by 162 days.

(21) Appl. No.: 14/363,288

(22) PCT Filed: Dec. 21, 2012

(86) PCT No.: PCT/AU2012/001596

§ 371 (c)(1),
(2) Date: Jun. 5, 2014

(87) PCT Pub. No.: WO2013/091021

PCT Pub. Date: Jun. 27, 2013

(65) Prior Publication Data

US 2015/0055788 A1 Feb. 26, 2015

(30) Foreign Application Priority Data

Dec. 22, 2011 (AU) ................................ 2011905381
Jul. 17, 2012 (AU) ................................ 2012903050

(51) Int. Cl.
*A61F 11/06* (2006.01)
*G10K 11/16* (2006.01)
(Continued)

(52) U.S. Cl.
CPC .............. *H04R 3/002* (2013.01); *H04R 3/005* (2013.01); *G10L 21/0216* (2013.01);
(Continued)

(58) Field of Classification Search
CPC ..... H04R 3/005; H04R 3/002; H04R 2499/11; H04R 5/033; H04R 2410/07; H04R 25/407; G10L 2021/02165; G10L 21/0216
(Continued)

(56) References Cited

U.S. PATENT DOCUMENTS 6,882,736 B2 4/2005 Dickel et al.
7,082,204 B2 7/2006 Gustavsson
(Continued)

FOREIGN PATENT DOCUMENTS

JP 6-269084 9/1994
JP 2001-124621 5/2001
(Continued)

OTHER PUBLICATIONS

Extended European Search Report dated May 29, 2015 for corresponding European Patent Application No. 12859115.3, 6pp.
(Continued)

*Primary Examiner* — Paul S Kim
(74) *Attorney, Agent, or Firm* — Lewis Roca Rothgerber Christie LLP

(57) ABSTRACT

A method of processing digitized microphone signal data in order to detect wind noise. First and second sets of signal samples are obtained simultaneously from two microphones. A first number of samples in the first set which are greater than a first predefined comparison threshold is determined. A second number of samples in the first set which are less than the first predefined comparison threshold is determined. A third number of samples in the second set which are greater than a second predefined comparison threshold is determined. A fourth number of samples in the second set which are less than the second predefined comparison threshold is determined. If the first number and second
(Continued)

number differ from the third number and fourth number to an extent which exceeds a predefined detection threshold, e.g. as determined by a Chi-squared test, then an indication that wind noise is present is output.

25 Claims, 23 Drawing Sheets

(51) Int. Cl.

| | |
|---|---|
| ***H03B 29/00*** | (2006.01) |
| ***H04R 3/00*** | (2006.01) |
| *G10L 21/0216* | (2013.01) |
| *H04R 5/033* | (2006.01) |
| *H04R 25/00* | (2006.01) |

(52) U.S. Cl.
CPC .... *G10L 2021/02165* (2013.01); *H04R 5/033* (2013.01); *H04R 25/407* (2013.01); *H04R 2410/07* (2013.01); *H04R 2499/11* (2013.01)

(58) Field of Classification Search
USPC ........................................................ 381/71.1
See application file for complete search history.

(56) References Cited

U.S. PATENT DOCUMENTS

| | | | |
|---|---|---|---|
| 7,171,008 B2 | 1/2007 | Elko | |
| 7,174,023 B2 | 2/2007 | Ozawa | |
| 7,305,099 B2 | 12/2007 | Gustavsson | |
| 7,340,068 B2 | 3/2008 | Petersen et al. | |
| 7,499,554 B2 | 3/2009 | Gustavsson | |
| 2005/0078842 A1 | 4/2005 | Vonlanthen et al. | |
| 2006/0120540 A1 | 6/2006 | Luo | |
| 2007/0030987 A1 | 2/2007 | Roeck et al. | |
| 2007/0030989 A1 | 2/2007 | Kates | |
| 2009/0238369 A1 | 9/2009 | Ramakrishnan et al. | |
| 2011/0103615 A1 | 5/2011 | Sun | |
| 2011/0135126 A1 | 6/2011 | Gozen | |
| 2012/0121100 A1* | 5/2012 | Zhang | G10L 21/0208 381/71.1 |
| 2012/0148067 A1 | 6/2012 | Petersen et al. | |

FOREIGN PATENT DOCUMENTS

| | | |
|---|---|---|
| WO | WO 2010/063660 A2 | 6/2010 |
| WO | WO 2011/006496 A1 | 1/2011 |

OTHER PUBLICATIONS

International Search Report for PCT/AU2012/001596 mailed Mar. 15, 2013, 5pp.

Written Opinion for PCT/AU2012/001596 mailed Mar. 15, 2013, 7 pp.

Kates, James M.; "Digital Hearing Aids"; Chapter 6: Wind Noise; Plural Publishing; 2008; pp. 147-173.

Zakis, Justin A.; "Wind noise at microphones within and across hearing aids at wind speeds below and above microphone saturation"; J. Acoust. Soc. Am.; 129; 6; Jun. 2011; pp. 3897-3907.

* cited by examiner

Chi-square WND - Bluetooth Headset (21 mm) - Block=16

4 m/s wind
6 m/s wind
8 m/s wind
FF Male
FF Female
NF Male
NF Female
WND Output
Time (s)
0
1
2
3
4
5
6
7
8
9
10
11
12
13
14

Correlation WND - Bluetooth Headset (21 mm) - Block=16

4 m/s wind
6 m/s wind
8 m/s wind
FF Male
FF Female
NF Male
NF Female
WND Output
Time (s)
-0.5
0.0
0.5
1.0
1.5
2.0
2.5
0
1
2
3
4
5
6

Diff/Sum WND - Bluetooth Headset (21 mm) - Block=16

4 m/s wind
6 m/s wind
8 m/s wind
FF Male
FF Female
NF Male
NF Female
WND Output
Time (s)
0
1
2
3
4
5
6
7
8

Far-Field Tone Sweep - Bluetooth Headset (21 mm) - Block=16
Cross/Auto Correlation
Difference/Sum
Chi-squared WND Output
Frequency (Hz)
100
1000
-1
0
1
2
3
4

Mouth Tone Sweep - Bluetooth Headset (21 mm) - Block=16

Chi-square WND (minimum) - Bluetooth Headset (21 mm) - Block=16

Chi-square WND - Smart Phone (120 mm) - Block=16
WND Output
Time (s)
4 m/s wind
6 m/s wind
8 m/s wind
FF Male
FF Female
NF Male
NF Female
RX Male
RX Female Correlation WND - Smart Phone (120 mm) - Block=16
WND Output
Time (s)
4 m/s wind
6 m/s wind
8 m/s wind
FF Male
FF Female
NF Male
NF Female
RX Male
RX Female Mouth Tone Sweep - Smart Phone (120 mm) - Block=16

Cross/Auto Correlation
Difference/Sum
Chi-squared
WND Output
8
7
6
5
4
3
2
1
0
-1
-2
-3
100
1000
Frequency (Hz)

Chi-square WND - Smart Phone (120 mm) - Block=32

4 m/s wind
6 m/s wind
8 m/s wind
FF Male
FF Female
NF Male
NF Female
RX Male
RX Female
WND Output
28
26
24
22
20
18
16
14
12
10
8
6
4
2
0
0
1
2
3
4
5
6
Time (s)

Correlation WND - Smart Phone (120 mm) - Block=32

4 m/s wind
6 m/s wind
8 m/s wind
FF Male
FF Female
NF Male
NF Female
RX Male
RX Female
WND Output
Time (s)
3.0
2.5
2.0
1.5
1.0
0.5
0.0
-0.5
0
1
2
3
4
5
6

Diff/Sum WND - Smart Phone (120 mm) - Block=32

4 m/s wind
6 m/s wind
8 m/s wind
FF Male
FF Female
NF Male
NF Female
RX Male
RX Female
WND Output
Time (s)
6
5
4
3
2
1
0
0
1
2
3
4
5
6

Chi-square WND output (1000 Hz BPF)

WND Output
Time (s)
Quiet
1.5 m/s wind
3 m/s wind
6 m/s wind
12 m/s wind
Female speech
Male speech
Near-Field tone
2320
2310
2330
2340

Chi-square WND output (5000 Hz BPF)

WND Output
Time (s)
Quiet
1.5 m/s wind
3 m/s wind
6 m/s wind
12 m/s wind
Female speech
Male speech
Near-Field tone
2420
2430
2410

Stepped Far-Field Tone Sweep
1000 Hz BPF
5000 Hz BPF

WND Output
4.0
3.5
3.0
2.5
2.0
1.5
1.0
0.5
0.0
1000
2000
3000
4000
5000
6000
7000
8000
Frequency (Hz)

Chi-square WND output (250 Hz FFT bin)

Quiet
1.5 m/s wind
3 m/s wind
6 m/s wind
12 m/s wind
Female speech
Male speech
Near-Field tone
WND Output
0.7
0.6
0.5
0.4
0.3
0.2
0.1
0.0
0
1
2
3
4
5
6
7
Time (s)

Chi-square WND output (750 Hz FFT bin)

Quiet
1.5 m/s wind
3 m/s wind
6 m/s wind
12 m/s wind
Female speech
Male speech
Near-Field tone
WND Output
Time (s)
0.0
0.1
0.2
0.3
0.4
0.5
0.6
0.7
0
1
2
3
4
5
6
7

Chi-square WND output (1000 Hz FFT bin)

Quiet
1.5 m/s wind
3 m/s wind
6 m/s wind
12 m/s wind
Female speech
Male speech
Near-Field tone
WND Output
Time (s)
0.0
0.1
0.2
0.3
0.4
0.5
0.6
0.7
0
1
2
3
4
5
6
7

Chi-square WND output (4000 Hz FFT bin)

Quiet
1.5 m/s wind
3 m/s wind
6 m/s wind
12 m/s wind
Female speech
Male speech
Near-Field tone
WND Output
Time (s)
0.0
0.1
0.2
0.3
0.4
0.5
0.6
0.7
0
1
2
3
4
5
6
7

Chi-square WND output (7000 Hz FFT bin)

Quiet
1.5 m/s wind
3 m/s wind
6 m/s wind
12 m/s wind
Female speech
Male speech
Near-Field tone
WND Output
Time (s)
0.0
0.1
0.2
0.3
0.4
0.5
0.6
0.7
0
1
2
3
4
5
6
7

Stepped Far-Field Tone Sweep

WND Output
0.7
0.6
0.5
0.4
0.3
0.2
0.1
0.0
2462
2464
2466
1000
2000
3000
4000
5000
6000
7000
8000
Frequency (Hz)

METHOD AND APPARATUS FOR WIND NOISE DETECTION

CROSS-REFERENCE TO RELATED APPLICATIONS

This application is a national phase application under 35 U.S.C. §371 of International Application No. PCT/AU2012/001596 filed on Dec. 21, 2012 which claims the benefit of Australian Provisional Patent Application No. 2011905381 filed 22 Dec. 2011, and Australian Provisional Patent Application No. 2012903050 filed 17 Jul. 2012, the contents of which are incorporated herein by reference in their entirety.

TECHNICAL FIELD

The present invention relates to the digital processing of signals from microphones or other such transducers, and in particular relates to a device and method for detecting the presence of wind noise or the like in such signals, for example to enable wind noise compensation to be initiated or controlled.

BACKGROUND OF THE INVENTION

Wind noise is defined herein as a microphone signal generated from turbulence in an air stream flowing past microphone ports, as opposed to the sound of wind blowing past other objects such as the sound of rustling leaves as wind blows past a tree in the far field. Wind noise can be objectionable to the user and/or can mask other signals of interest. It is desirable that digital signal processing devices are configured to take steps to ameliorate the deleterious effects of wind noise upon signal quality. To do so requires a suitable means for reliably detecting wind noise when it occurs, without falsely detecting wind noise when in fact other factors are affecting the signal.

Previous approaches to wind noise detection (WND) assume that non-wind sounds are generated in the far field and thus have a similar sound pressure level (SPL) and phase at each microphone, whereas wind noise is substantially uncorrelated across microphones. However, for non-wind sounds generated in the far field, the SPL between microphones can substantially differ due to localized sound reflections, room reverberation, and/or differences in microphone coverings, obstructions, or location. Substantial SPL differences between microphones can also occur with non-wind sounds generated in the near field, such as a telephone handset held close to the microphones. Differences in microphone output signals can also arise due to differences in microphone sensitivity, i.e. mismatched microphones, which can be due to relaxed manufacturing tolerances for a given model of microphone, or the use of different models of microphone in a system.

The spacing between the microphones causes non-wind sounds to have different phase at each microphone sound inlet, unless the sound arrives from a direction where it reaches both microphones simultaneously. In directional microphone applications, the axis of the microphone array is usually pointed towards the desired sound source, which gives the worst-case time delay and hence the greatest phase difference between the microphones.

When the wavelength of a received sound is much greater than the spacing between microphones, the microphone signals are fairly well correlated and previous WND methods may not falsely detect wind at low frequencies. However, when the received sound wavelength approaches the microphone spacing, the phase difference causes the microphone signals to become less correlated and non-wind sounds can be falsely detected as wind. The greater the microphone spacing, the lower the frequency above which non-wind sounds will be falsely detected as wind, i.e. the greater the portion of the audible spectrum in which false detections will occur. Given that wind noise at hearing-aid microphones can extend from below 100 Hz to above 8000 Hz depending on hardware configuration and wind speed, it is desirable for wind noise detection to operate satisfactorily throughout much if not all of the audible spectrum, so that wind noise can be detected and suitable suppression means activated only in sub bands where wind noise is problematic. False detection may also occur due to other causes of phase differences between microphone signals, such as localized sound reflections, room reverberation, and/or differences in microphone phase response or inlet port length.

Existing approaches to WND include three techniques referred to herein as the correlation method, the difference method and the difference-sum method. These are discussed briefly below.

First, in the correlation method set out in U.S. Pat. No. 7,340,068 two microphone signals are low pass filtered (fc=1 kHz) then the cross-correlation and auto-correlation are calculated with the following equation:

$$D = \frac{\sum_{n=-k}^{k} x(n)y(n-l)}{\sum_{n=-k}^{k} x^2(n-l)} \quad (1)$$

where x(n) and y(n) are samples of the output of microphones x and y, respectively, 1=0 for zero correlation lag, and k=0 for single-sample correlation or k>0 for correlation over a block of samples. The detector output D should theoretically approach 1 for non-wind sounds, where x(n) and y(n) should be similar, and should tend toward 0 for wind noise, where x(n) and y(n) should be dissimilar. The detector output is passed through a low-pass smoothing filter, and wind is detected when the smoothed D<0.67, and preferably when smoothed D<0.5.

Second, in the difference method for WND described in U.S. Pat. No. 6,882,736, the absolute value of the difference between two microphone signals is calculated using the equation:

$$D=|x(n)-y(n)| \quad (2)$$

where x(n) and y(n) are samples of the output of microphones x and y, respectively. The detector output, D, should theoretically approach 0 for a non-wind source, where x(n) and y(n) should be highly correlated, and increase for wind noise, where x(n) and y(n) should be less similar. The value of D is passed through a low-pass smoothing filter, and wind is detected when the smoothed value exceeds a threshold.

Third, in the difference-sum method described in U.S. Pat. No. 7,171,008, the ratio between the difference and the sum power values of two microphone signals is calculated with the equation:

$$D = \frac{\sum_n |x(n)-y(n)|^2}{\sum_n |x(n)+y(n)|^2} \quad (3)$$

where x(n) and y(n) are samples of the output of microphones x and y, respectively, over a period of time that may be one sample or a block of samples. The detector output, D, should theoretically approach 0 for a far-field source, where x(n) and y(n) should be similar, and D should tend towards 1 for wind noise, where x(n) and y(n) should be dissimilar.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word “comprise”, or variations such as “comprises” or “comprising”, will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of processing digitized microphone signal data in order to detect wind noise, the method comprising:

obtaining from a first microphone a first set of signal samples;

obtaining from a second microphone a second set of signal samples arising substantially contemporaneously with the first set;

determining a first number of samples in the first set which are greater than a first predefined comparison threshold, and determining a second number of samples in the first set which are less than the first predefined comparison threshold;

determining a third number of samples in the second set which are greater than a second predefined comparison threshold, and determining a fourth number of samples in the second set which are less than the second predefined comparison threshold; and determining whether the first number and second number differ from the third number and fourth number to an extent which exceeds a predefined detection threshold, and if so outputting an indication that wind noise is present.

The first and second sets of signal samples may comprise wideband time domain samples obtained substantially directly from the respective microphones. Alternatively the first and second sets of signal samples may comprise sub-band time domain samples reflecting a particular spectral band of a wideband microphone signal, for example as may be obtained by lowpass, highpass or bandpass filtering the microphone signals. In some embodiments the first and second sets of signal samples may comprise spectral magnitude data, for example as may be obtained by performing a Fourier transform upon the microphone signals, e.g. a fast Fourier transform. In still further embodiments the first and second sets of signal samples may comprise power data, complex signal data or other forms of signal data in which wind noise gives rise to supra-detection threshold differences in the data values arising in the first and second sets.

The first predefined comparison threshold in many embodiments will be the same as the second predefined comparison threshold. In some embodiments the first and second predefined comparison thresholds may each be zero. In other embodiments the first and second predefined comparison thresholds may be set to a value, or set to respective values, which is or are between digital quantisation levels, so that no sample value will ever equal the comparison threshold. In further embodiments the first and second predefined comparison thresholds may each be the mean of selected past and/or present signal samples. In yet further embodiments, the first and second predefined comparison thresholds may be given values which account for a DC component in the signal samples, whether a continuous or intermittent DC component. In other embodiments the first and second predefined comparison thresholds may be equal to the mean for each bin of one or multiple frames of FFT data. In still further embodiments the first and second predefined comparison thresholds may be any other suitable value for the data samples obtained. In alternative embodiments of the invention the first predefined comparison threshold may differ from the second predefined comparison threshold. For example in such alternative embodiments the first predefined comparison threshold may be configured such that samples valued zero are counted as a positive number, while the second predefined comparison threshold may be configured such that samples valued zero are counted as a negative number, or vice versa if more appropriate and/or convenient for the application and/or implementation platform.

Throughout this specification, reference to a number of “positive” samples is to be understood as referring to samples which are greater than, i.e. positive relative to, the corresponding predefined comparison threshold. The corresponding meaning is to be given to references to a number of “negative” samples. Thus, when the corresponding predefined comparison threshold is equal to zero, the conventional meaning of positive and negative will apply.

The step of determining whether the number of positive and negative samples in the first set differ from the number of positive and negative samples in the second set to an extent which exceeds a predefined detection threshold may be performed by applying a Chi-squared test. In such embodiments, if the Chi-squared calculation returns a value close to zero or below the predefined detection threshold then an indication of the absence of wind noise may be output, whereas if the Chi-squared calculation returns a value greater than or equal to the detection threshold an indication of the presence of wind noise may be output. In such embodiments, for a sample block size of 16 and microphone spacing of 12 mm the detection threshold may be in the range of 0.5 to about 4, more preferably in the range of 1 to 2.5. For a sample block size of 16 and microphone spacing of 120 mm the detection threshold may be in the range of about 2 to about 10, more preferably in the range of 3 to 8 or more preferably in the range of about 5 to 7. However an appropriate detection threshold may be considerably different in other embodiments having a different block size and/or microphone spacing and/or device. The detection threshold may be set to a level which is not triggered by light winds which are deemed unobtrusive, such as wind below 1 or 2 $m \cdot s^{-1}$. Moreover, in such embodiments the output of the Chi-squared calculations, or more generally the extent to which the first number and second number differ from the third number and fourth number, may be used to estimate the strength of the wind in otherwise quiet conditions, or the degree of which wind noise dominates over other sounds.

In alternative embodiments the step of determining whether the number of positive and negative samples in the first set differ from the number of positive and negative samples in the second set to an extent which exceeds a predefined detection threshold may be performed by any other suitable statistical test for comparing multiple sets of binary or categorical data, such as McNemar's test or the Stuart-Maxwell test.

The first and second microphones may be mounted on a behind-the-ear (BTE) device, such as a shell of a cochlear implant BTE unit, or a BTE, in-the-ear, in-the-canal, completely-in-canal, or other style of hearing aid. Alternatively the first and second microphones may be part of a telephony headset or handset, or other audio devices such as cameras, video cameras, tablet computers, etc. The signal may be sampled at 8 kHz, 16 kHz or 48 kHz, for example. Some embodiments may use longer block lengths for higher sampling rates so that a single block covers a similar time frame. Alternatively, the input to the wind noise detector may be down sampled so that a shorter block length can be used (if required) in applications where wind noise does not need to be detected across the entire bandwidth of the higher sampling rate. The block length may be 16 samples, 32 samples, or other suitable length.

The method may in some embodiments further comprise obtaining from a third microphone, or additional microphone, a respective set of signal samples. In such embodiments a comparison of the number of positive and negative samples in respective sample sets obtained from the three or more microphones may be made. For example a Chi-squared test may be applied to three or more microphone signal sample sets by use of an appropriate 3×2, or 4×2 or larger, observation matrix and expected value matrix.

According to a further aspect the present invention provides a computing device configured to carry out the method of the first aspect.

According to another aspect the present invention provides a computer program product comprising computer program code means to make a computer execute a procedure for processing digitized microphone signal data in order to detect wind noise, the computer program product comprising computer program code means for carrying out the method of the first aspect.

In preferred embodiments of the invention, each microphone signal is preferably high pass filtered, for example by pre-amplifiers or ADCs, to remove any DC component, such that the sample values operated upon by the present method will typically contain a mixture of positive and negative numbers. However, in alternative embodiments where the sample values have a non-zero quiescent value the present invention may be applied by referring the comparison thresholds to the quiescent value, i.e. by determining (a) the number of samples falling above the quiescent value, and (b) the number of samples falling below the quiescent value. The invention may similarly be applied by reference to any chosen comparison threshold values suitable for the sampled data being processed.

By considering only the sign of each sample relative to a comparison value and not the magnitude, the method of the present invention effectively ignores magnitude differences between microphone signals, and so it is robust against non-wind causes of such differences, such as near-field sound sources, localized sound reflections, room reverberation, and differences in microphone coverings, obstructions, location, or sensitivity. It also largely ignores phase differences between microphone signals, since the number of positive and negative samples per signal are counted over a block of samples, in contrast to other methods which calculate the sample-by-sample correlation between signals and which are highly sensitive to phase and amplitude differences between microphone signals.

In some embodiments of the invention a single count within each sample set from each microphone may be performed. For example, for each sample set one of the following may be counted:

how many of the samples are positive,
how many of the samples are negative,
how many of the samples exceed a threshold, or
how many of the samples are less than a threshold.

In such embodiments the extent to which the single count for the first set of signal samples differs from the single count for the second set of signal samples may be used to trigger an output indicating the presence of wind noise. For example, this could be via using the counts as indices to a look-up table of pre-calculated Chi-squared values, as inputs to a simplified Chi-squared equation that may take advantage of known constants for a particular application, or as inputs to another suitable statistical test, such as a binomial test.

It is noted that the presence of a non-wind noise sound which is at a frequency which produces approximately an odd number of half periods in the sample block or an odd number of samples per period may, depending on the phase difference between the microphones, lead to the first and second number differing from the third and fourth number to a significant extent even in the absence of wind noise. Such a scenario may thus lead to a false detection of wind noise, depending on the detection threshold being used. However, the risk of such a false detection may in some embodiments be addressed by determining whether the first number and second number differ from the fourth number and third number, respectively, and outputting an indication that wind noise is present only if this difference also exceeds the predefined detection threshold. By swapping the values of the third number and fourth number, or conducting an equivalent inversion of the data or sample counts of one of the sample sets, such embodiments improve robustness to non-wind noise sounds at such problematic frequencies. Such embodiments are referred to herein as a "minimum" technique, for example as a "minimum Chi-squared wind noise detection" technique. Alternative embodiments may be made more computationally efficient by avoiding two Chi-squared calculations, by making the third number alternatively equal the number of negative samples in the second set and the fourth number alternatively equal the number of positive samples in the second set, and then performing a single Chi-squared calculation with the value of third number (i.e. original or alternative value) that differs the least from the value of the first number. These differences are calculated by subtracting each of the original and alternative values of the third number from the first number. It is noted that the original and alternative values of the third number can only differ from the first number by the same extent when the first number and original third number are both equal to half of the number of samples in each block, in which case the difference is zero and the Chi-squared value is also zero.

BRIEF DESCRIPTION OF THE DRAWINGS

An example of the invention will now be described with reference to the accompanying drawings, in which:

FIGS. 24*a* to 24*e* show the outputs of the Chi-squared methods for pre-recorded input signals processed by 250, 750, 1000, 4000 and 7000 Hz FFT bins, while

ABBREVIATIONS

ADC: Analog to Digital Converter
BTE: Behind The Ear
CI: Cochlear Implant
DC: Direct Current
FIR: Finite Impulse Response
HA: Hearing Aid
HATS: Head And Torso Simulator
IIR: Infinite Impulse Response
SNR: Signal to Noise Ratio
SPL: Sound Pressure Level
WND: Wind Noise Detection

DESCRIPTION OF THE PREFERRED EMBODIMENTS

Figure 1:
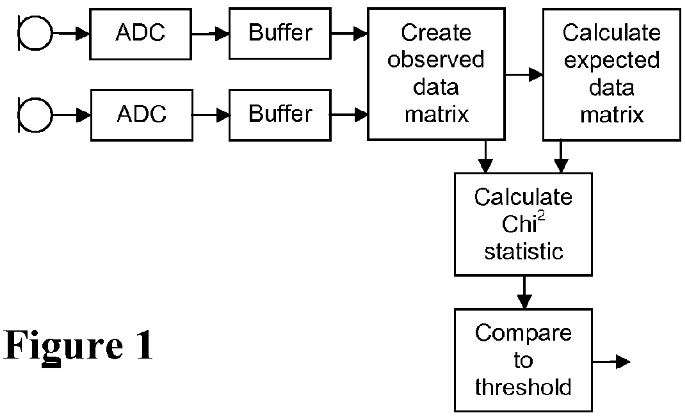
FIG. 1 is a system schematic illustrating a Chi-squared wind noise detector of one embodiment of the invention operating in the time domain.

The WND method of the present embodiment, referred to as the Chi-Squared ($\chi^2$) WND method, applies a statistical test to establish the level of independence between two or more audio signals. The Chi-squared method of this embodiment comprises three steps: 1) The construction of an Observed data matrix from a block of samples of each microphone signal; 2) The construction of an Expected data matrix; and 3) The calculation of the Chi-squared statistic from the Observed and Expected data matrices. These steps are shown FIG. 1 for the case of two microphones. While the Chi-squared WND method of FIG. 1 is described for simplicity for the case of two microphones, it is to be noted that in alternative embodiments this method can be applied for use with three or more microphone signals.

The input data are a block of samples of each microphone signal, as follows:

$$X=[x_1\ x_2\ \ldots\ x_m]$$

$$Y=[y_1\ y_2\ \ldots\ y_m] \tag{4}$$

where X and Y are blocks of front and rear microphone samples, respectively, of length m samples. The buffering of samples for block-based processing is common in DSP systems, so advantageously the Chi-squared WND method may not require any additional buffering operations and can work with a wide range of buffer lengths. Since pre-amplifiers or ADCs typically high-pass filter the microphone signals to remove any DC component, the sample values are typically a mixture of positive and negative numbers that tend towards zero as the sound level decreases.

An Observed data matrix, O, is constructed, and contains the number of positive and negative values in the block of samples of each microphone signal as follows:

$$O = \begin{bmatrix} \sum_{n=1}^{m} POS(x_n) & \sum_{n=1}^{m} NEG(x_n) \\ \sum_{n=1}^{m} POS(y_n) & \sum_{n=1}^{m} NEG(y_n) \end{bmatrix} \quad (5)$$

where POS is a function that returns the number of positive samples (values ≥0), and NEG is a function that returns the number of negative samples (values <0). In practical two-compliment DSP systems, a value of zero has a positive sign bit and thus may most easily be classed as a positive value. Zero values could be defined as either positive or negative values for the purposes of the Chi-squared WND method, provided that the definition was consistent for a given implementation. As can be seen in equation (5) each row of the Observed matrix O corresponds to a different microphone, while the columns one and two show the number of positive and negative samples, respectively.

An Expected data matrix, E, is calculated from the data in the Observed data matrix, O, as follows:

$$E_{ij} = \frac{\sum_{k=1}^{c} O_{ik} \cdot \sum_{k=1}^{r} O_{kj}}{N} \quad (6)$$

where r and c are the number of rows and columns, respectively, in the Observed matrix, O, and N is the sum of all elements in the Observed matrix, O. N is thus a constant that is equal to the number of microphones multiplied by the block length.

The Observed and Expected matrices are used to calculate the Chi-Squared statistic, $\chi^2$, as follows:

$$X^2 = \sum_{i=1}^{r} \sum_{j=1}^{c} \frac{(O_{ij} - E_{ij})^2}{E_{ij}} \quad (7)$$

where $\chi^2$ is the sum of the squared and normalized differences between elements of the Observed and Expected data matrices. The value of $\chi^2$ is zero when the ratio of positive to negative samples is the same for both microphones, which is approximated with non-wind sounds. The value of $\chi^2$ increases above zero as the ratio of positive to negative samples differs across microphones, which occurs as the microphone signals become less similar which can be a result of wind noise.

By considering only the sign of each sample and not the magnitude, the Chi-squared method of the present embodiment effectively ignores magnitude differences between microphone signals, and so it is robust against non-wind causes of such differences, such as near-field sound sources, localized sound reflections, room reverberation, and differences in microphone coverings, obstructions, location, or sensitivity (mismatched microphones).

The Chi-squared method of this embodiment is also largely robust against phase differences because it does not attempt to compare the microphone signals on a sample-by-sample basis. For non-wind sounds, the robustness depends on the relationship between the wavelength, size of the phase shift, and block length used in the application. In contrast to previous methods, the robustness against phase differences can increase at high frequencies depending on the relationship between the block length and the microphone spacing. For example, if the block length is an integer number of wavelengths of a stationary sinusoidal signal, then the number of positive and negative samples will be the same for any phase shift that is an integer number of samples. When the wavelength is greater than the block length, the effect of a phase difference varies from block to block, and has the greatest effect around zero crossings and can have zero effect between zero crossings. A smoothing filter may thus be used to even out block-to-block variations in the wind score output in order to compensate for such effects.

As a practical example of the robustness against phase differences, in hearing-aid applications a typical microphone spacing of up to 20 mm results in a delay of up to 59 μs between microphones (assuming the speed of sound is 340 m/s), which translates to a phase difference of up to 0.94 samples with a typical sampling rate of 16 kHz. Such a phase difference has a minimal effect on the $\chi^2$ statistic with typical block lengths of 16 to 64 samples.

The following example is provided to give further understanding of how the Chi-Squared WND method of this embodiment works in practice. The example is for two microphones experiencing wind noise, and a block length of 16 samples. A block of samples is shown below for each microphone:

$$X=[-1\ 1\ 2\ 0\ -2\ -5\ -3\ -1\ -7\ -3\ -1\ 2\ -3\ -5\ -1\ -2]$$

$$Y=[-1\ -3\ -2\ 2\ 5\ 3\ 4\ 1\ 0\ -3\ 2\ 7\ 1\ 0\ 3\ -2] \quad (8)$$

The number of positive and negative samples in each block are counted and used to construct the Observed matrix, O, as per equation (5) above:

$$O = \begin{bmatrix} 4 & 12 \\ 11 & 5 \end{bmatrix} \quad (9)$$

where the number of positive and negative samples are shown in the first and second columns, respectively, with one row for each microphone. By definition, the sum of each row is equal to the block length (16 in this case). The Expected matrix, E, is calculated from the Observed data matrix, O, as per equation (6) above:

$$E = \begin{bmatrix} 7.5 & 8.5 \\ 7.5 & 8.5 \end{bmatrix} \quad (10)$$

The Expected data matrix, E, has the same structure as the Observed data matrix, O, and both matrices are used to calculate the Chi-squared statistic, $\chi^2$, as per equation (7) above:

$$X^2 = \frac{(4-7.5)^2}{7.5} + \frac{(12-8.5)^2}{8.5} + \frac{(11-7.5)^2}{7.5} + \frac{(5-8.5)^2}{8.5} = \frac{(-3.5)^2}{7.5} + \frac{(3.5)^2}{8.5} + \frac{(3.5)^2}{7.5} + \frac{(-3.5)^2}{8.5} = 6.15 \quad (11)$$

The value of the Chi-squared statistic, $\chi^2$, is substantially greater than zero, indicating the presence of wind noise.

In preferred embodiments of the invention, some computational steps are simplified based on known constants. For example, the Expected matrix, E, requires the calculation of products of row and column sums of the Observed matrix, O. Since the row sums of the Observed matrix, O, are always equal to the block length, B, and N is always equal to the number of microphones M multiplied by the block length, the calculation of the Expected matrix, E, can be simplified as follows:

$$E_{ij} = \frac{\sum_{k=1}^{c} O_{ik} \cdot \sum_{k=1}^{r} O_{kj}}{N} = \frac{\sum_{k=1}^{c} O_{ik} \cdot B}{B \cdot M} = \frac{\sum_{k=1}^{c} O_{ik}}{M} \quad (12)$$

The previous Chi-squared example shows that the rows of the Expected matrix, E, are identical to each other, which reduces the computational requirement to the calculation of one value for each of the j columns of the Expected matrix, E.

The calculation of the $\chi^2$ value can also be simplified, and the calculation of the Expected matrix, E, can be incorporated into this calculation as follows:

$$X^2 = \sum_{i=1}^{r} \sum_{j=1}^{c} \frac{\left( O_{ij} - \frac{\sum_{k=1}^{c} O_{ik}}{M} \right)^2}{\frac{\sum_{k=1}^{c} O_{ik}}{M}} \quad (13)$$

Thus, for each element of the Observed matrix, O, the squared difference between it and its column mean is divided by its column mean. In a given column, the squared difference will be the same for both rows, which further reduces the required computational load to calculate the $\chi^2$ statistic. The above is just one example of how the computational load may be optimized for the application, and further optimizations may be achieved in other embodiments. In some applications, it may be desirable to use a look-up table of pre-calculated $\chi^2$ values that could be indexed with the positive or negative sample count value of each microphone signal. In yet another embodiment, Equation 13 can be further simplified to the following for the case of two microphones:

$$X^2 = (O_{11} - O_{21})^2 \times \left( \left( \frac{1}{O_{11} + O_{21}} \right) + \left( \frac{1}{N - (O_{11} + O_{21})} \right) \right) \quad (14)$$

Figure 2:
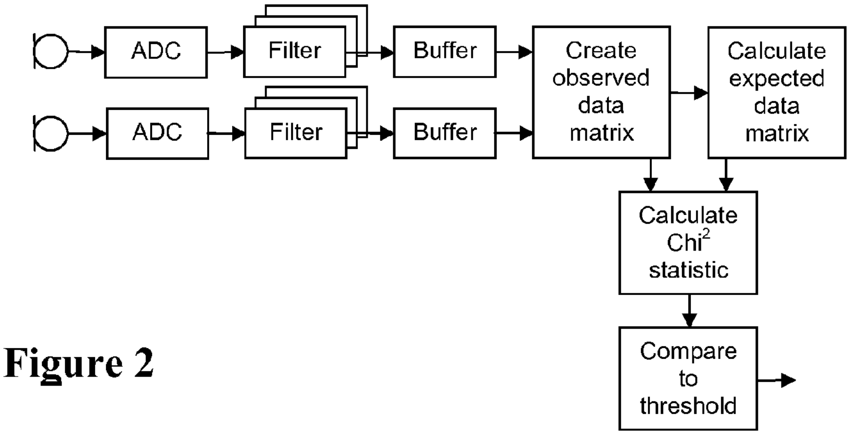
FIG. 2 is a system schematic illustrating a sub-band implementation of a Chi-squared WND method operating on the outputs of matching time-domain filters, in accordance with another embodiment of the invention.

In another embodiment the method of the present invention is implemented on a sub-band basis. The Chi-squared WND method described above is used to process the buffered output of a time-domain digital filter, which could be a band-pass, low-pass, or high-pass filter. FIG. 2 shows an example of sub-band WND with a time-domain filter bank. Within each sub-band the operation of the method is as described above in the embodiment of FIG. 1 and is not repeated here. It is noted that the most suitable comparison and/or detection thresholds may differ in different sub bands and for different applications, which may be due to factors such as the microphone positioning, spacing, and/or phase matching, and/or the characteristics of wind noise and other sounds at different frequencies.

Figure 3:
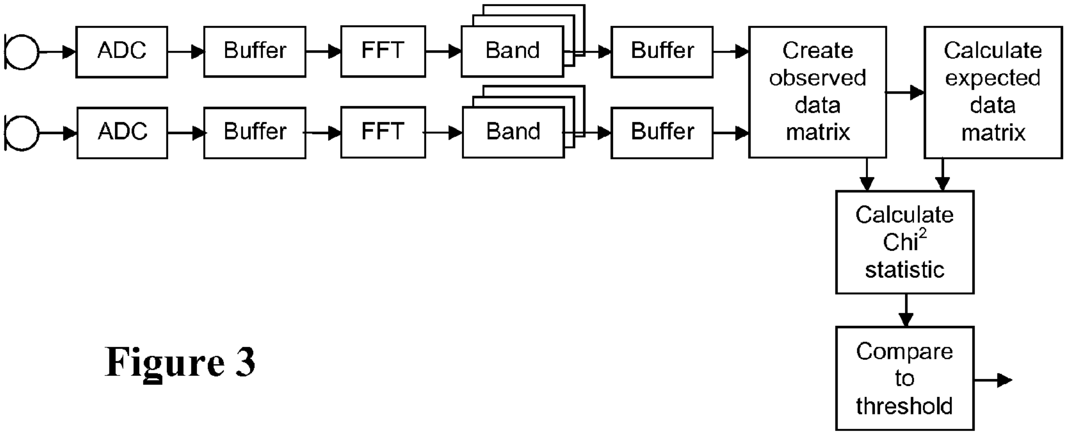
FIG. 3 is a system schematic illustrating a sub-band implementation of a Chi-squared WND method operating on FFT output data, in accordance with yet another embodiment of the invention.

In yet another embodiment, shown in FIG. 3, the Chi-squared WND method operates on Fast Fourier Transform (FFT) data. In this embodiment, a FFT is performed on a block of samples of each microphone signal, and FFT output data are then buffered across multiple blocks for each FFT bin. The buffered FFT output data could be magnitude, power, or the real and/or imaginary components of the complex FFT output. The magnitude or power data may be in dB units in some applications. Instead of counting the number of positive and negative samples in a block, positive and negative FFT output values are counted across blocks in the FFT output data buffer. In this respect, the FFT output is treated as a frequency-domain sample of the microphone signal. Since raw FFT magnitude or power values cannot be negative, they need to be processed in a way that can result in positive or negative values. For example, the data in the FFT output buffers could be processed to be: 1) FFT magnitude or power data adjusted so that the data in each buffer has a zero mean value; or 2) FFT magnitude or power difference data, which show difference values between successive FFTs. As an alternative to 1) above, the comparison threshold for each FFT bin and microphone may be adaptively set to the mean (or other suitable value) of past or present buffered FFT magnitude or power data. Although the real or imaginary components of the raw FFT data can have positive and negative values without further processing, the application of processing options 1) and 2) above may be beneficial since these components are more sensitive to amplitude and phase differences between microphone signals. These exemplary alternatives result in data that show the variation in sound level over time (with one-block resolution). Thus, the data do not show level differences between microphones that are due to differences in microphone sensitivity, near-field effects, or any other constant (or in practice, slowly time-varying) cause of level differences between the microphone signals.

Compared with time-domain samples, FFT data are relatively insensitive to phase differences between microphone signals, since they represent the average magnitude or power over a block of samples. Phase has the greatest effect on FFT power estimates when the wavelength is significantly greater than the block length (i.e. analysis window), and least effect when the wavelength is much smaller than the block length. These beneficial attributes of the FFT data used to construct the Observed matrix, O, are in addition to the inherent robustness of the Chi-squared WND method against magnitude and phase differences between microphone signals. For non-wind sounds, the short-term variation in FFT bin level over time is similar between microphones, which results in Chi-squared values of around zero (i.e. wind not detected). For wind noise, short-term variation in level differs between microphones, which results in larger values of the Chi-squared statistic (i.e. wind detected). FFT bins may be grouped to form wider bands, and the magnitude or power values calculated for each band and then used to detect wind noise in that band.

To illustrate the efficacy of the embodiment of FIG. 1, the method of that embodiment was evaluated by using it to test a number of representative recordings. The recordings were of microphone output signals obtained from behind-the-ear (BTE) devices with a range of input stimuli. The stimuli were generated from a far-field loudspeaker, a near-field phone handset, or a wind machine. The devices were BTE shells from commercial cochlear implant (CI) and hearing aid (HA) products, each containing two microphones spaced approximately 10-15 mm apart. The microphones were not perfectly matched, but the mismatch would be typical for these types of microphones (1-3 dB). The devices were mounted on the pinna (outer ear) of a Head And Torso Simulator (HATS) that was placed in a sound booth for all but the near-field recordings. The near-field recordings were obtained by holding a phone handset at the BTE device in free space in a quiet office. The microphone signals were recorded by a high-SNR, 32-bit sound card with a sampling rate of approximately 16 kHz. Table 1 summarizes the stimuli, devices, equipment and recording conditions:

TABLE 1 pre-recorded input stimuli

| Stimulus | Device | Setup |
|---|---|---|
| Stepped Tone Sweep | BTE CI shell | HATS, sound booth, far-field tones from in front. |
| Near Field 1 kHz Tone | BTE CI shell | Quiet room, phone handset near front microphone. |
| Quiet (Mic. noise) | BTE CI shell | HATS, sound booth. |
| Female speech | BTE CI shell | HATS, sound booth, far-field speech from in front. |
| Male speech | BTE CI shell | HATS, sound booth, far-field speech from in front. |
| Wind at 1.5 m/s | BTE CI shell | HATS, sound booth, wind from in front. |
| Wind at 3.0 m/s | BTE CI shell | HATS, sound booth, wind from in front. |
| Wind at 6.0 m/s | BTE CI shell | HATS, sound booth, wind from in front. |
| Wind at 12.0 m/s | BTE HA shell | HATS, sound booth, wind from in front. |

The recordings were each approximately 10 seconds in duration, except for the far-field stepped tone sweep which consisted of 31 pure tones from 1.0 to 7.664 kHz (in multiplicative steps of 1.0718) with a duration of 4 seconds per tone. The stepped tone sweep also included unintended level differences between microphone signals of up to 10 dB, which were due to localized pinna reflections and/or room reflections and lead to some non-smoothness in the data shown in FIG. 7. The near-field 1 kHz tone resulted in a 12.2 dB level difference between the microphone signals. The speech was presented at 70 dBA (measured at the ear). The wind speed increased in factors of two since this is theoretically equivalent to 12-dB steps of wind-noise level. The 12 m/s recording was chosen as an example where the microphone outputs were clearly saturated at the electrical clipping level of both microphones, since this extreme may be a potential failure mode for WND algorithms.

Figure 4:
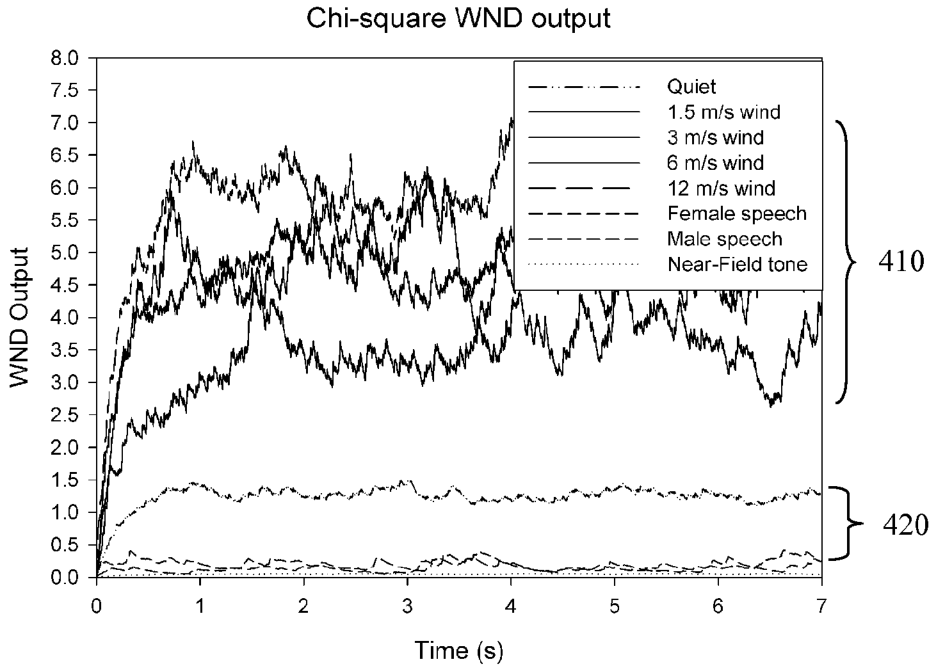
FIG. 4 illustrates the Chi-squared WND scores produced by the embodiment of FIG. 1 for respective pre-recorded input signals.

The WND algorithm of the embodiment of FIG. 1 was implemented in Matlab/Simulink, and used to process non-overlapping, consecutive blocks of 16 samples of each microphone recording. The output of the WND algorithm was processed by an IIR filter (b=[0.004]; a=[1 −0.996], it being noted that other filter types and coefficients could be used) to smooth out any jitter-like changes in the WND algorithm output that may exist from one block to another, and hence give a more consistent output for a constant input stimulus. FIG. 4 shows the output of the Chi-squared WND method for the respective pre-recorded input signals in this system.

In FIG. 4 it can be seen there is clear separation between the wind stimuli WND scores (grouped at 410) and the non-wind stimuli WND scores 420. In group 420 the WND output produced by the method of this embodiment of this invention is less than 0.5 for the speech and near-field stimuli, and less than 1.5 for the uncorrelated microphone noise. After the smoothing filter has settled, in group 410 it can be seen that the WND output score for wind noise is consistently greater than 2.5-3.0 for very light wind (1.5 m/s) and increases up to 5 or 6 with increasing wind speed. Thus a suitable detection threshold above which the WND score is taken to indicate the presence of wind noise could be 2.5 in applications where wind at 1.5 m/s and above needs to be detected, or 3.5 in applications where wind at 3 m/s and above needs to be detected. A wind speed of 1.5 m/s would typically cause very little wind noise and may not be audible, and so in many applications it may be desirable not to detect and suppress such light wind. It is noted that the absolute value of the WND scores and thus the appropriate threshold(s) will change for different sample block sizes. It is also noted that the WND scores for wind noise mixed with non-wind sounds may lie between those grouped at 410 and 420, which is advantageous in that the detection threshold may be set to correspond to the most appropriate ratio of wind noise to other sounds for the application, which may be based on factors such as the perception of wind noise above other sounds, or the requirements of processing that follows wind-noise suppression means. Moreover, the thresholds could also be refined for different smoothing filters, since heavier smoothing will result in a more consistent WND output score, which could allow the detection threshold to be increased, albeit at the expense of a slower reaction time of the filter in response to a change in wind conditions. It is also noted that the output of the Chi-squared method is low (near zero) for microphone noise, so an input level threshold is not necessarily required for WND as is the case for some other methods. Nevertheless, alternative embodiments could use a relatively low Chi-squared threshold to reliably detect low-speed wind, combined with an input level threshold to set the SPL above which it is desired for wind to be detected. In such embodiments the use of an input level threshold allows detection to be more closely related to the loudness of the wind noise, since the wind-noise level at a given wind speed is affected by factors such as the wind angle of incidence (all of the shown data are for wind from in front), the mechanical design of the device, microphone locations, the location of obstructions near the microphones (e.g. outer ear) that can act as wind shields or wind noise generators, and so on. In such embodiments, both the Chi-squared threshold and input level threshold need to be exceeded for wind to be detected.

To compare the performance of this embodiment of the invention, the WND algorithms of the prior art correlation method and difference-sum method discussed in the preceding were implemented in Matlab/Simulink, and similarly used to process non-overlapping, consecutive blocks of 16 samples of each microphone recording shown in Table 1 above. The output of each WND algorithm was again processed by an IIR filter (b=[0.004]; a=[1 −0.996]).

Figure 5:
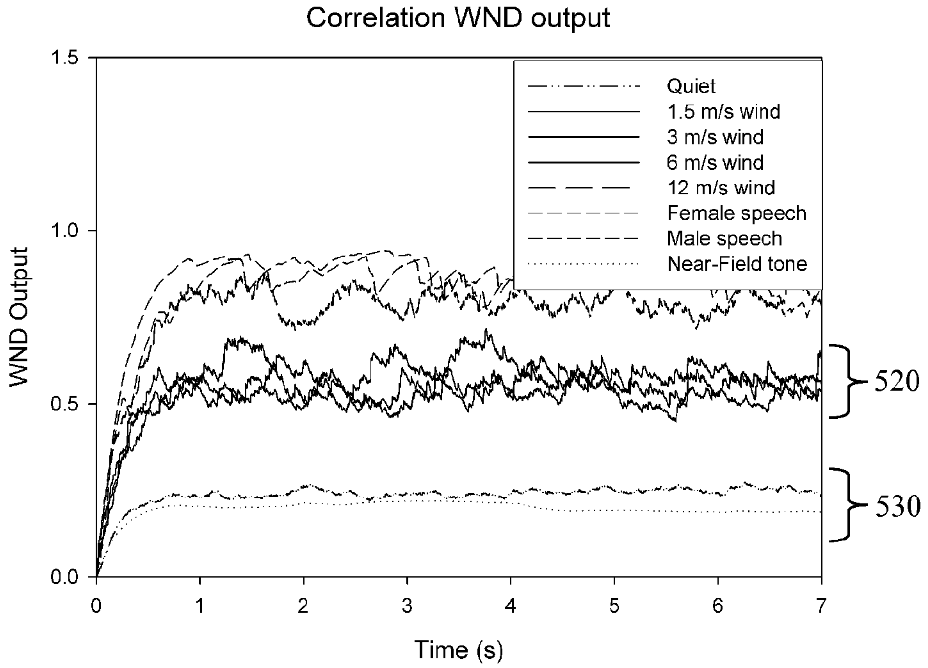
FIG. 5 illustrates the WND scores produced by the prior art correlation method for the pre-recorded input signals.

FIG. 5 shows the results for the prior art correlation WND method of U.S. Pat. No. 7,340,068, discussed in the preceding. The output for speech is close to 1.0, as expected, and wind noise is generally lower (approximately 0.5 as shown at 520). However, 12 m/s wind that saturates the microphones tends to yield a similar output as for speech, which could lead to the correlation WND method failing to detect strong wind. Moreover the output for uncorrelated microphone noise and a near-field tone, indicated at 530, are in the wind range of values, and could thus be incorrectly classified as wind, although the microphone noise could be distinguished from wind noise by applying the additional step of an input level threshold.

Figure 6:
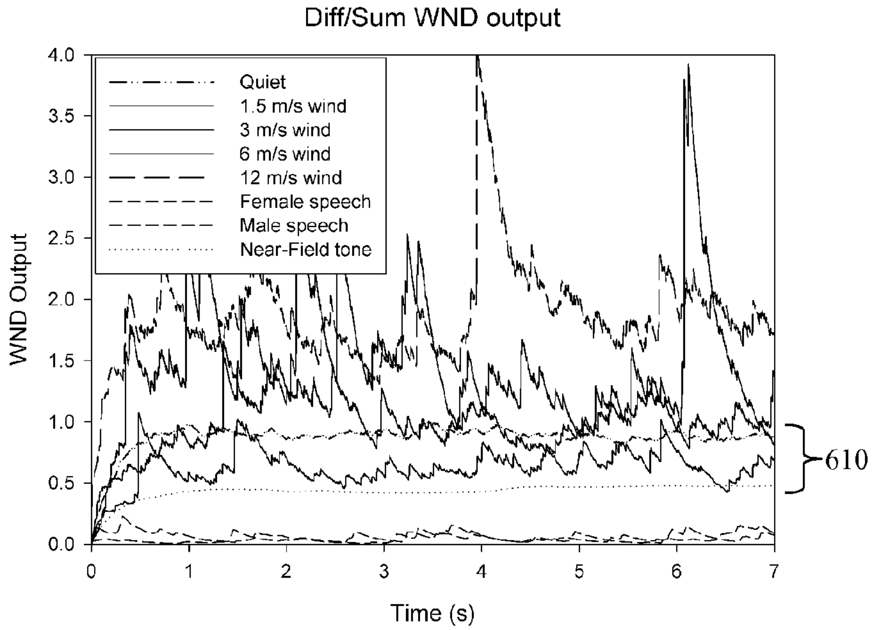
FIG. 6 illustrates the WND scores produced by the prior art Diff/Sum WND method for the pre-recorded input signals.

FIG. 6 shows the output of the prior art Diff/Sum WND method of U.S. Pat. No. 7,171,008, discussed in the preceding. The Diff/Sum WND output is approximately zero for speech, as expected, and the output increases with wind speed. However, in the region indicated by 610, the near-field tone and 1.5 m/s wind cannot be distinguished, nor can the uncorrelated microphone noise from the 3.0 m/s wind. The latter two inputs could likely be distinguished from each other by applying the additional step of an input level threshold.

Figure 7:
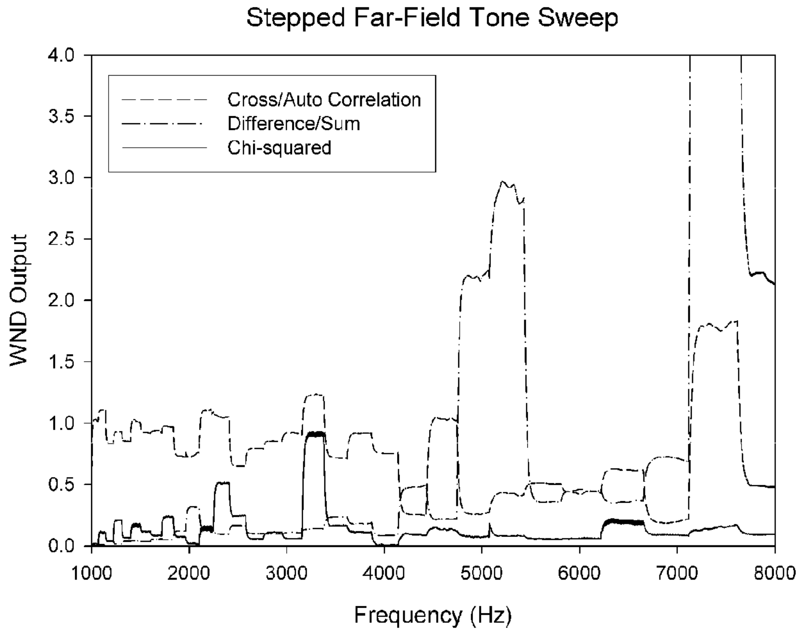
FIG. 7 illustrates the WND scores produced by the embodiment of FIG. 1 and the prior art WND methods, in response to a pre-recorded stepped tone sweep input.

FIG. 7 compares the WND method of the embodiment of FIG. 1 to the prior art correlation and difference/sum WND methods, and shows the output of the WND methods implemented in Matlab/Simulink in response to the microphone output signals for a stepped tone sweep input. The Chi-squared method is robust against the tones, with output values which are less than 1.0 across the entire band tested, and which are largely less than 0.25. These values are well below the range of 2.5-4.0 as is output for weak 1.5 m/s wind as shown in FIG. 4, thus enabling the WND method of FIG. 1 to differentiate between such tone inputs and wind noise.

In contrast, FIG. 7 shows that the correlation WND method generally diverges from its non-wind output (a value about 1) to wind outputs (values less than 0.67 or 0.5) with increasing frequency, which would lead to false detection of wind noise in response to such tones. Similarly, the difference/sum WND method generally diverges from its non-wind output (a value about 0) to wind outputs (values tending towards 1) with increasing frequency, which would also lead to false detection of wind noise in response to such tones.

While the preceding embodiments of this invention suggest some thresholds for the Chi-squared detector, it is noted that there will be some flexibility and variability in setting appropriate thresholds. This is because the output of the Chi-squared WND would scale up with larger block sizes and be affected by microphone spacing and positioning, and the threshold can be set fairly arbitrarily to make the WND trigger at the desired wind speed or ratio of the level of wind noise to other sounds, if desirable for the application.

The efficacy of the present invention across the entire band of FIG. 7 is particularly advantageous to a sub-band wind-noise detector such as that of FIG. 2 or 3, which should preferably function appropriately at distinguishing wind noise from other inputs at all frequencies in the hearing-aid bandwidth up to the Nyquist rate (typically up to 8-12 kHz).

The audio signals are typically microphone output signals, but any other audio source could be used. Typical applications would be hearing aids, cochlear implants, headsets, handsets, video cameras, or any other medical or consumer device where wind noise needs to be detected. To assess the performance of the embodiment of FIG. 1 in such other hardware devices, the sensitivity of the aforementioned WND methods to falsely detecting pure tones as wind was investigated. Each method was implemented in a MATLAB simulation, and sinusoidal input stimuli for the two microphones were generated in MATLAB. The rear microphone signal was delayed in phase relative to the front microphone according to the specified microphone spacing (assuming the speed of sound is 340 m/s). Typical examples of real-time, DSP audio products were modelled, as shown in Table 2.

TABLE 2

| Product | Microphone Spacing | Sampling rate | Block size |
|---|---|---|---|
| Generic: ideal microphone spacing | 0 mm | 16 kHz | 16 samples |
| Hearing aid | 12 mm | 16 kHz | 16 samples |
| Bluetooth headset | 20 mm | 8 kHz | 16 samples |
| Smart phone 1 | 150 mm | 8 kHz | 16 samples |
| Smart phone 2 | 150 mm | 8 kHz | 32 samples |

The WND outputs were calculated for frequencies from 10 Hz to half of the sampling rate in 10-Hz steps. For each frequency, the average output for each WND method was calculated over 100 successive blocks of samples, and the averaged values are shown in FIGS. 8 to 17. The averaging approximates a low-pass filter that would typically be implemented to smooth out block-to-block variations in WND method outputs.

In addition, the above analyses were repeated for a level difference of 9.5 dB between the microphones (rear microphone signal lower). Given the $1/r^2$ relationship in sound power from distance from the source, this approximated a near-field sound source that was 3 times further away from one microphone than the other.

For the ideal case of 0 mm microphone spacing (i.e. both microphones in phase), no WND methods falsely detect the tone as wind at any frequency, with the outputs of the prior art difference-sum, difference, and correlation methods being equal to 0, 0, and 1, respectively, (correctly indicating no wind noise) and the present Chi-squared WND method output being equal to zero (correctly indicating no wind noise).

Figure 8:
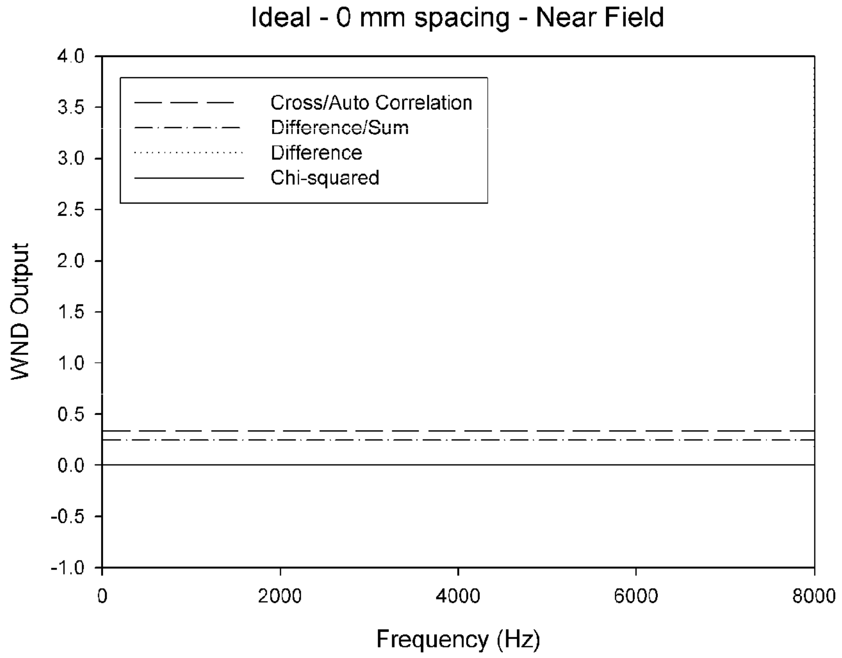
FIG. 8 illustrates the WND scores produced by a simulation of the embodiment of FIG. 1 and the prior art WND methods in response to simulated tone inputs from 10 Hz to half of the sampling rate in 10-Hz steps, for the case of both microphones in phase but with the presence of 9.5 dB near-field effect.

However, for the case of 0 mm microphone spacing (i.e. both microphones in phase), but with the presence of the described 9.5 dB near-field effect, the output of the Chi-squared WND method is totally unaffected by the level difference between microphones whereas the other methods are significantly affected in the simulation, as shown in FIG. 8, and may thus result in incorrect indications of wind-noise. The output of the Difference method in this case was >4 and therefore not visible in FIG. 8.

Figure 9:
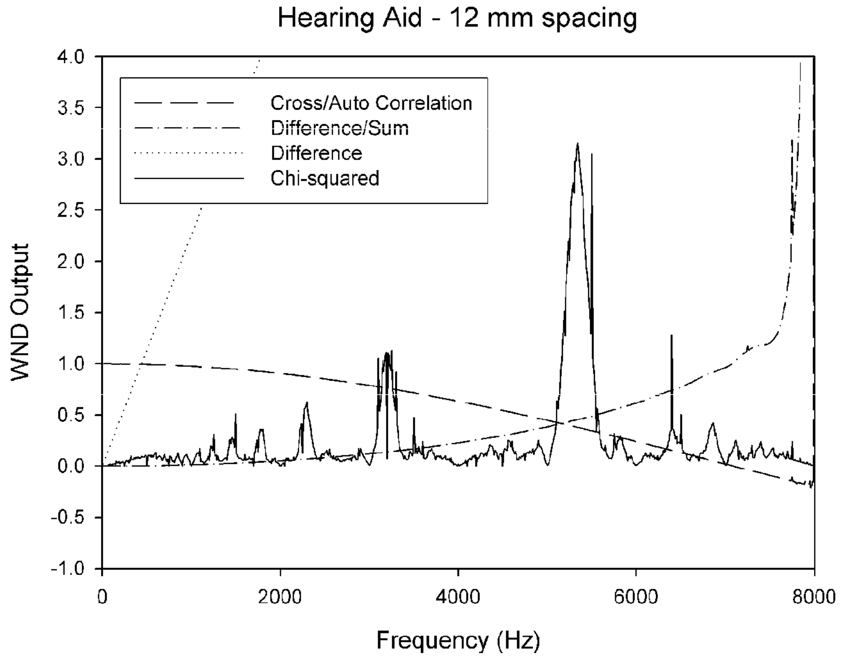
FIG. 9 illustrates the WND scores produced by a simulation of the embodiment of FIG. 1 and the prior art WND methods, in response to simulated far-field tone inputs from 10 Hz to half of the sampling rate in 10-Hz steps, for a typical hearing aid.

FIG. 9 shows the simulated WND output values for a typical hearing aid (as per Table 2). It can be seen that the previous WND methods falsely detect the tone as wind at higher frequencies. The Chi-squared method of the embodiment of FIG. 1 is more robust, although around 5.4 kHz its output is relatively high, although not necessarily above a nominated wind detection threshold which as seen in FIG. 4 may be selected to be as high as about 3.5 in some embodiments. The behaviour of the Chi-squared WND score at 5.4 kHz is due to the tone having a period of approximately 3 samples, and the microphone spacing causing a phase shift of approximately 0.56 samples. As a result, approximately two thirds of the front microphone samples are positive, while approximately two thirds of the rear microphone samples are negative, which explains the relatively high output of the Chi-squared WND method around 5.4 kHz. It is to be noted that by around 5.4 kHz or well before, all three prior art methods are also suffering significant degradations.

It is further noted that the artefact at 5.4 kHz in the present Chi-squared method seen in FIG. 9 can be counteracted by repeating the WND processing with the front or rear microphone signal inverted, which changes the phase relationship between the microphone signals, and then taking the lower of the two WND output magnitude values as the WND output to pass through a smoothing filter. This approach was applied to the simulation of all four methods to produce the graph of FIG. 10, in which it can be seen that there is little change in the relatively poor robustness of the previous WND methods, whereas the Chi-squared WND method's robustness against high-frequency tones has significantly increased. This approach may therefore be beneficial in some embodiments of the present invention, in applications where the additional computational load is justified. Computational load may be further reduced by swapping the positive and negative sample count values for one microphone signal instead of re-counting them with an inverted signal, and only running the $\chi^2$ calculations the second time if the score will be reduced (i.e. if the sample counts among microphones become more similar). Computational load may be even further reduced as previously described by calculating alternative third and fourth numbers that correspond to the number of negative and positive samples relative to the second comparison threshold, and running a single $\chi^2$ calculation for the version of the third number (i.e. original or alternative) that differs the least from the first number.

Figure 10:
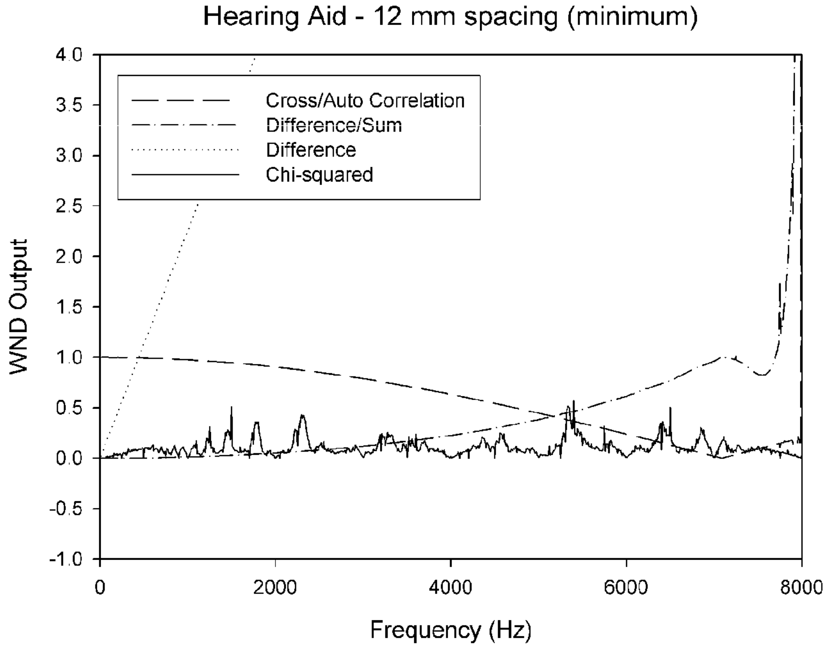
FIG. 10 illustrates the WND scores of FIG. 9 when improved by scores obtained by a simulation of inverting the positive and negative counts for one signal.
Figure 11:
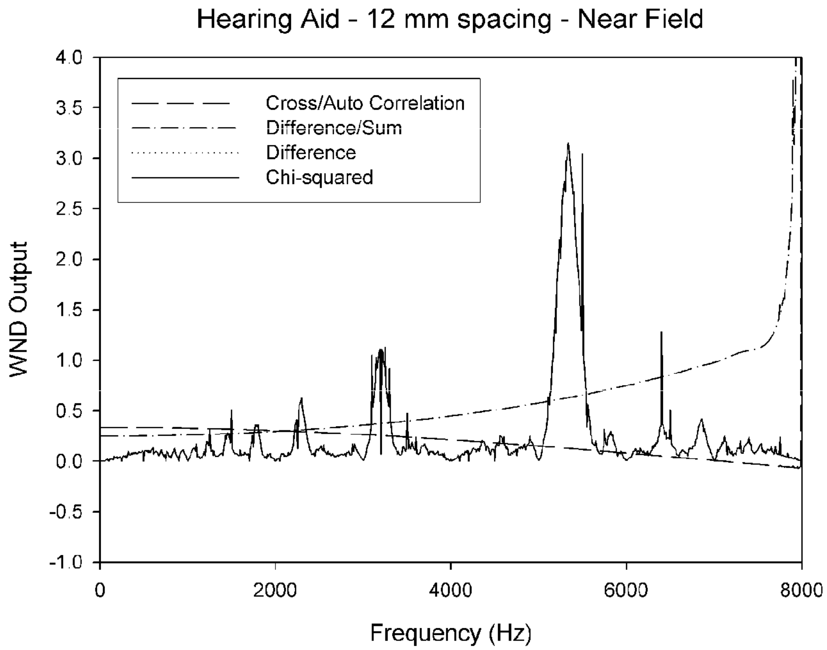
FIG. 11 illustrates the WND scores produced by a simulation of the embodiment of FIG. 1 and the prior art WND methods, in response to simulated near-field tone inputs varying by 9.5 dB from 10 Hz to half of the sampling rate in 10-Hz steps, for a typical hearing aid.

FIG. 11 shows the simulated output scores of the three prior art WND methods and the WND method of the present invention when applied by a hearing aid as set out in Table 2, and when a 9.5 dB reduction is applied to the rear microphone signal level. The Chi-squared WND output is unaffected by the level difference between the microphone signals, while the other methods are clearly adversely affected. Again, it is noted that the artefact around 5.4 kHz in the Chi-squared WND scores may be below a detection threshold (and thus not trigger false detections) and/or may be addressed by repeating the score calculation using an inverted signal, in a corresponding manner as discussed in the preceding with reference to FIG. 10.

Figure 12:
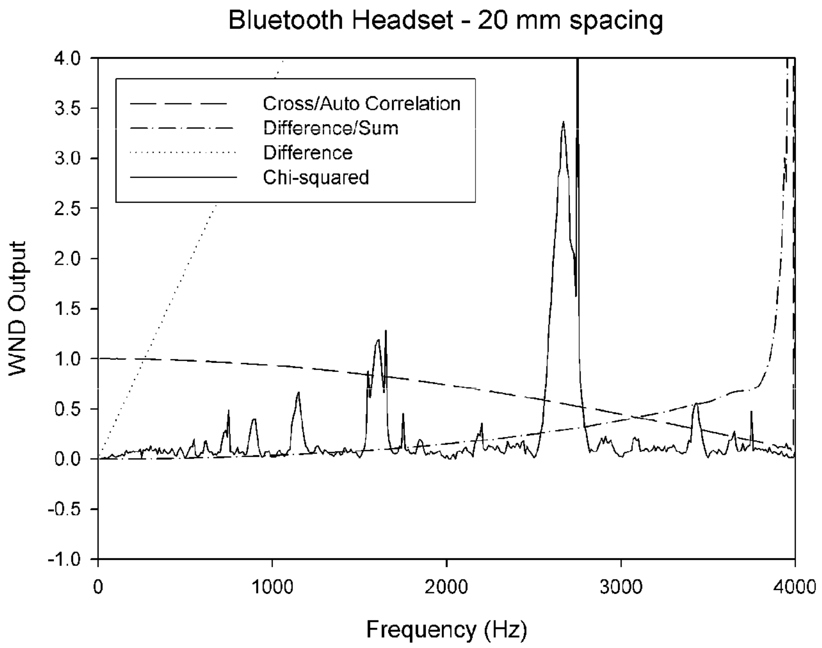
FIG. 12 illustrates the WND scores produced by a simulation of the embodiment of FIG. 1 and the prior art WND methods, in response to simulated far-field tone inputs from 10 Hz to half of the sampling rate in 10-Hz steps, for a typical Bluetooth headset.

The robustness of the prior art WND methods and the WND method of the embodiment of FIG. 1, for the simulated example of a typical Bluetooth headset as per Table 2, is shown in FIG. 12. Again, the Chi-squared method of the embodiment of FIG. 1 is similarly robust to tone inputs, except on a halved frequency scale due to the lower sampling rate of the Bluetooth headset. Again, it is noted that the artefact around 2.7 kHz in the Chi-squared WND scores, which is due to a half-sample delay between microphones with a pure-tone stimulus that has a three-sample period, may be below a detection threshold (and thus not trigger false detections) and/or may be addressed by repeating the score calculation using an inverted signal, in a corresponding manner as discussed in the preceding with reference to FIG. 10.

Figure 13:
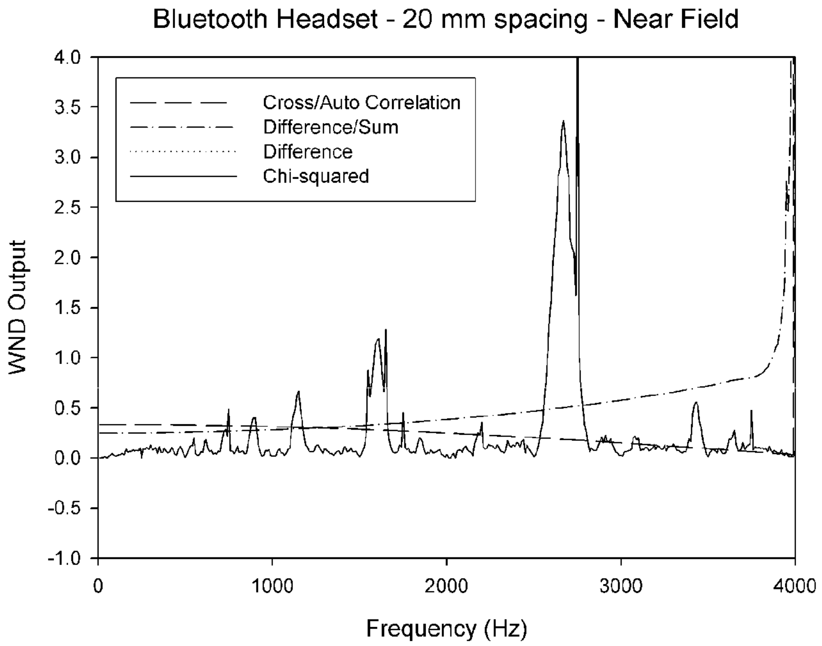
FIG. 13 illustrates the WND scores produced by a simulation of the embodiment of FIG. 1 and the prior art WND methods, in response to simulated near-field tone inputs varying by 9.5 dB from 10 Hz to half of the sampling rate in 10-Hz steps, for a typical Bluetooth headset.

The robustness of the prior art WND methods and the WND method of the embodiment of FIG. 1, for the simulated example of a typical Bluetooth headset as per Table 2 with a 9.5 dB level difference between the input signals, is shown in FIG. 13. Again, the Chi-squared method of the embodiment of FIG. 1 is robust to tone inputs. It is again noted that the artefact around 2.7 kHz in the Chi-squared WND scores may be below a detection threshold (and thus not trigger false detections) and/or may be addressed by repeating the score calculation using an inverted signal, in a corresponding manner as discussed in the preceding with reference to FIG. 10.

Thus, in the Bluetooth headset example of FIG. 13, the Chi-squared WND method is unaffected by level differences between microphones, while the other methods are clearly adversely affected and can falsely detect wind with a pure-tone input.

Figure 14:
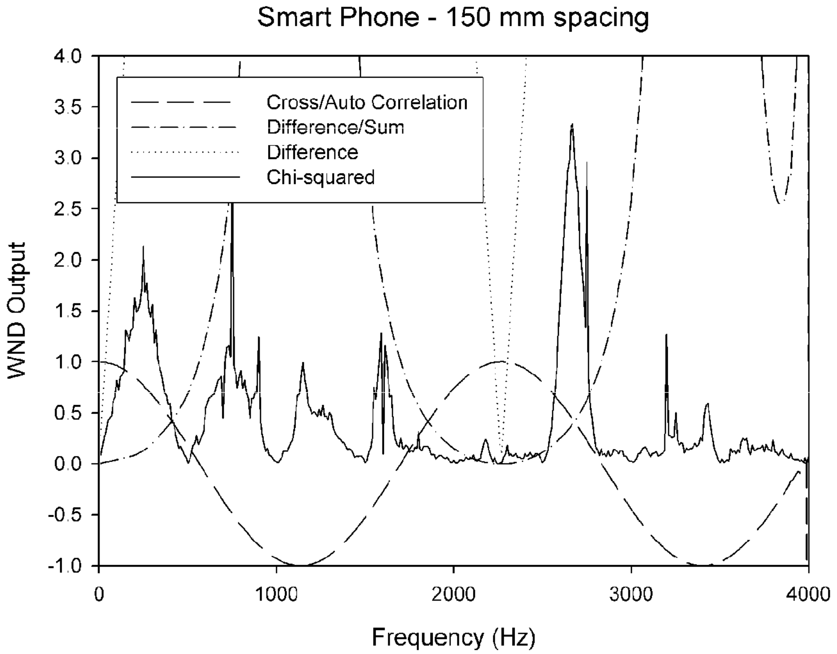
FIG. 14 illustrates the WND scores produced by a simulation of the embodiment of FIG. 1 and the prior art WND methods, in response to simulated far-field tone inputs from 10 Hz to half of the sampling rate in 10-Hz steps, for a typical smart-phone handset with 16 samples per block.

The robustness of the prior art WND methods and the WND method of the embodiment of FIG. 1, for the simulated example of a typical smart-phone handset with 16 samples per block as per Table 2, is shown in FIG. 14. The relatively large microphone spacing of 150 mm has generally worsened performance by substantially reducing the range of frequencies over which previous WND methods are robust against tones. The peaks in the Chi-squared WND scores below 2 kHz are at frequencies where there are approximately N+0.5 periods (N=0, 1, 2, etc) in the block length (i.e. 250 Hz, 750 Hz, 1250 Hz, etc). This is because if the block contains the entire first half of a sine-wave period (i.e. all samples positive), a phase shift will have a maximal effect on the ratio of positive to negative samples. The effect of the phase shift on the ratio of positive to negative samples tends to become smaller as the number of periods in the block length increases. With a microphone spacing of 150 mm and a sampling rate of 8 kHz, the phase delay between the two smart-phone handset microphones is up to 3.5 samples (depending on the direction of the sound). This compares with delays of less than one sample for typical hearing-aid and Bluetooth headset applications, which had a smaller effect on the ratio of positive to negative samples below 2 kHz. The effect of phase delay can be reduced or tuned for different applications by using a longer block size, since this makes the delay between microphones equal to a smaller percentage of the samples in the block. Moreover, most of the sub-2 kHz peaks in the chi-squared WND scores reach a value of only about 2.0, which as previously discussed may be below a detection threshold and thus such peaks may not trigger false detection of wind noise in the chi-squared WND detector. Additionally, the peaks in the Chi-squared WND detector may be reduced by repeating the score calculation using an inverted signal, in a corresponding manner as discussed in the preceding with reference to FIG. 10.

Figure 15:
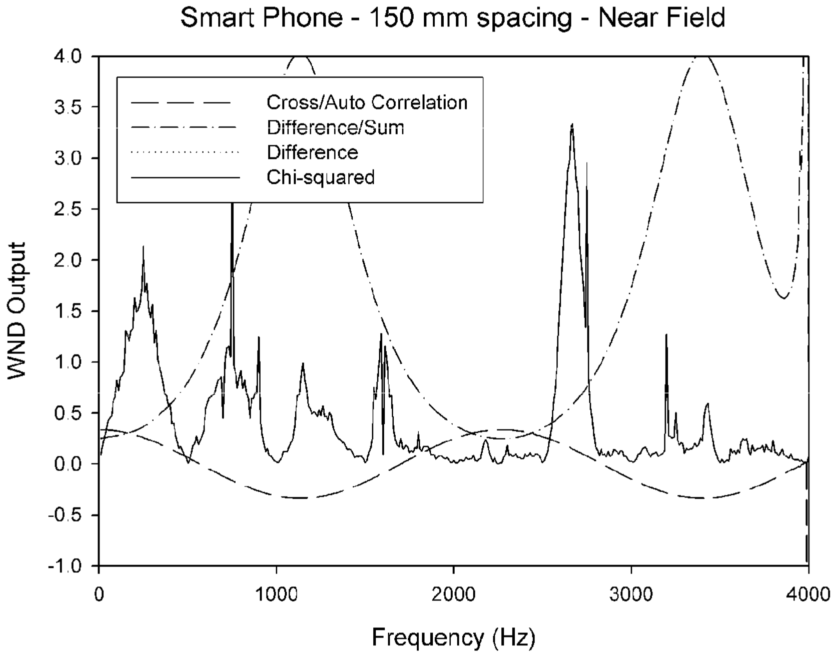
FIG. 15 illustrates the WND scores produced by a simulation of the embodiment of FIG. 1 and the prior art WND methods, in response to simulated near-field tone inputs varying by 9.5 dB from 10 Hz to half of the sampling rate in 10-Hz steps, for a typical smart-phone handset with 16 samples per block.

The robustness of the prior art WND methods and the WND method of the embodiment of FIG. 1, for the simulated example of a typical smart-phone handset with 16 samples per block as per Table 2, and with 9.5 dB level difference between the signals, is shown in FIG. 15. As for previous examples, the Chi-squared WND method is unaffected by level differences between microphones, while the other methods are clearly affected.

Figure 16:
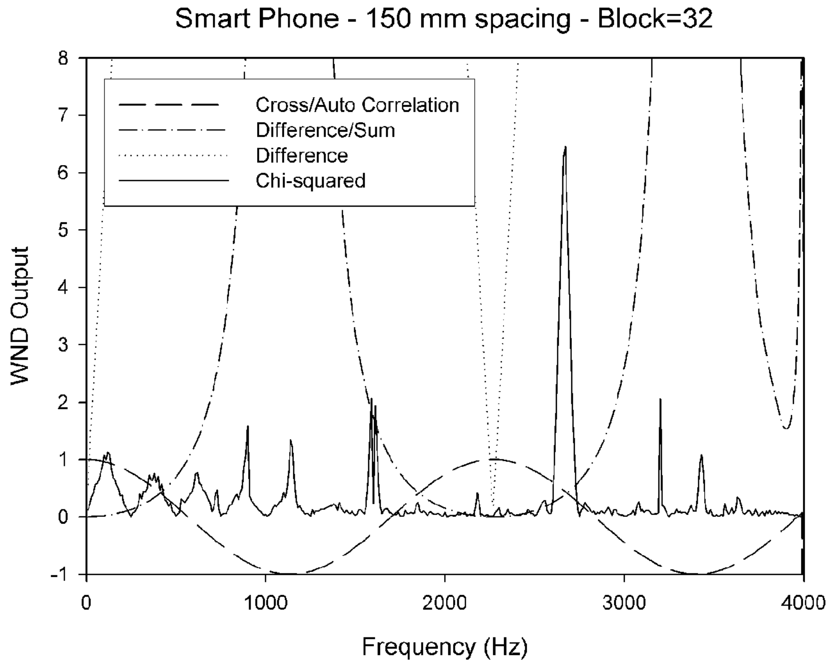
FIG. 16 illustrates the WND scores produced by a simulation of the embodiment of FIG. 1 and the prior art WND methods, in response to simulated far-field tone inputs from 10 Hz to half of the sampling rate in 10-Hz steps, for a typical smart-phone handset with 32 samples per block.

The robustness of the prior art WND methods and the WND method of the embodiment of FIG. 1, for the simulated example of a typical smart-phone handset with 32 samples per block as per Table 2, is shown in FIG. 16. Increasing the block size from 16 to 32 samples has the following effects on the Chi-squared WND:

1. The output will increase since more samples are being counted, so wind-detection thresholds will need to be adjusted accordingly.
2. The output is calculated less often, which will more than compensate for the processing of a greater number of samples during the initial counting step of the Chi-squared WND method.
3. In samples, the phase delay between microphones is a smaller percentage of the block length, so it will have a smaller effect on the output of the Chi-squared WND method for pure tones, as evidenced by the reduced peak heights in the Chi-squared WND scores in FIG. 16 as compared to FIG. 14 below approximately 1 kHz.

Compared with a block size of 16 samples, the low-frequency peaks in the Chi-squared WND output are substantially reduced, since the 3.5 sample delay between microphones is a smaller percentage of the number of samples in the 32-sample block. The peak around 2.7 kHz is larger due to the growth in numerical output due to the increase in block length, and hence the sample counts at the input of the Chi-squared WND method, however as per item (1) above the WND detection threshold will also have risen and so the peak at 2.7 kHz may still not lead to falsely triggering detection of wind noise. Additionally, the peaks in the Chi-squared WND detector may be reduced by repeating the score calculation using an inverted signal, in a corresponding manner as discussed in the preceding with reference to FIG. 10.

Figure 17:
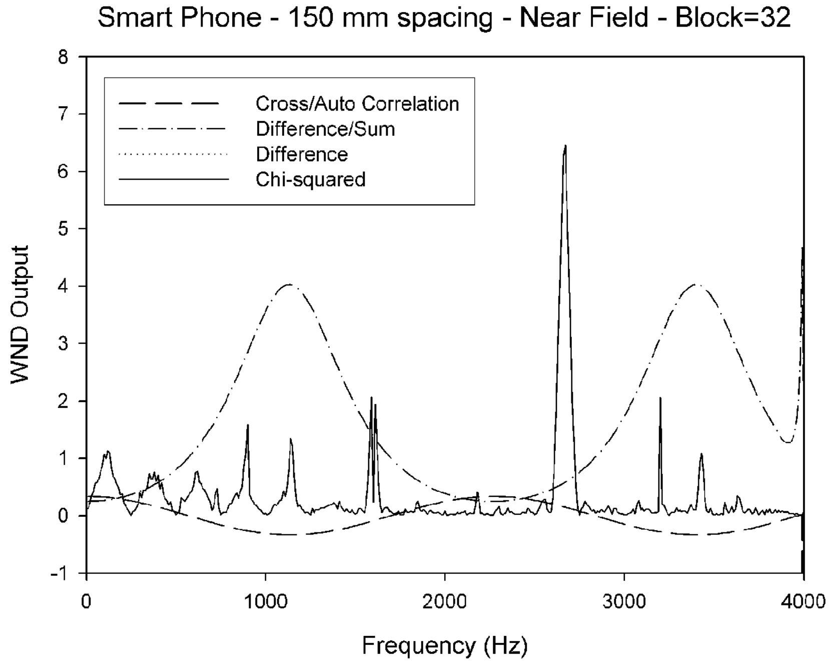
FIG. 17 illustrates the WND scores produced by a simulation of the embodiment of FIG. 1 and the prior art WND methods, in response to simulated near-field tone inputs varying by 9.5 dB from 10 Hz to half of the sampling rate in 10-Hz steps, for a typical smart-phone handset with 32 samples per block.

The robustness of the prior art WND methods and the WND method of the embodiment of FIG. 1, for the simulated example of a typical smart-phone handset with 32 samples per block as per Table 2, and with a 9.5 dB level difference between the input signals, is shown in FIG. 17. Once again, as for previous examples, the Chi-squared WND method is unaffected by level differences between microphones, while the other methods are clearly affected. As for the case of FIG. 16 the peak at 2.7 kHz may in some cases not lead to false triggering of detection of wind noise, and the peaks in the Chi-squared WND detector may optionally be reduced by repeating the score calculation using an inverted signal, in a corresponding manner as discussed in the preceding with reference to FIG. 10.

With regard to FIGS. 14-17 it is noted that a 150 mm microphone spacing for a smart phone is perhaps a worst-case scenario, and that significantly smaller microphone spacings may exist in such devices, with concomitant improvement in performance of the method of FIG. 1. Moreover, it is noted that these results for 150 mm microphone spacing may also apply to other devices such as video cameras which may have similar microphone spacing.

Thus, the simplification of input sampled data to sums of positive and negative sign values for each audio channel over a block of samples offers a number of benefits. The use of sign values provides robustness against magnitude differences which may arise in the signals for reasons other than wind, such as near field sounds or mismatched microphones. Collating the sign values over a block of time as opposed to correlations on a sample by sample basis improves robustness against typical phase differences arising from microphone spacing or phase response. Simplifying the sample data to binary values relative to zero or other suitable threshold permits use of the Chi-squared test, or other approach.

In alternative embodiments the Chi-squared calculations may be effected by a look-up table of pre-calculated Chi-squared values, should this improve computational efficiency, for example, or simplified Chi-squared equations that take advantage of constants such as the total number of samples per microphone per block. The comparison of the two blocks of samples may be performed in a subset of the audible frequency range for example by pre-filtering the signals. The WND scores are preferably smoothed, by a suitable FIR, IIR or other filter, to reduce frame-to-frame variations in the Chi-squared WND score for a steady-state input sound.

The efficacy of the WND method of the present invention when applied to phone handsets and headsets was further investigated. FIGS. 18 to 22 compare the output of the Chi-squared WND method of the present invention to the respective outputs of the previously discussed correlation, and difference-sum wind noise detection (WND) methods, using acoustic stimuli delivered to headsets and handsets placed on a head-and-torso-simulator (HATS) in a sound booth with each device in a typical use position.

The experiments reflected in FIGS. 18 to 22 assessed the following hardware/processing cases:

- Phone handset (120 mm microphone spacing) with block size=16 or 32 samples;
- Bluetooth headset (21 mm microphone spacing) with block size=16 samples.

In more detail, to obtain the results of FIGS. 19 and 20 a Bluetooth headset was modified so that its microphone signals were accessible via wires that exited the device near the ear (i.e. away from the microphone inlet ports). The two microphones were at typical positions for a Bluetooth headset, and were spaced 21 mm apart (typical spacing). To obtain the results of FIGS. 21 and 22 a dummy smart phone handset was modified in a similar way, with the wires exiting so that they did not go near the microphones, and therefore did not generate wind noise that reached the microphones. The two microphones were at the top (near the ear) and bottom (near the mouth) ends of the handset, and this resulted in a microphone spacing of 120 mm, which was considered a typical worst-case spacing for level and phase differences between microphone signals for this type of device.

For each headset and handset experiment, the device was placed on a head-and-torso-simulator (HATS) in a sound booth with each device in a typical use position. For each device, both microphone signals were simultaneously recorded by a high-quality sound card while presented with various acoustic input stimuli (as set out in Table 3 below). The recordings were stored as WAV files with a sampling rate of 8 kHz. The HATS was facing the source stimuli for all recordings (i.e. stimuli presented from directly in front of the HATS), which is the worst-case orientation for stimulus phase differences between microphones.

TABLE 3

| Stimulus | Device(s) |
|---|---|
| 4 m/s wind (10 seconds) | Headset & Handset |
| 6 m/s wind (10 seconds) | Headset & Handset |
| 8 m/s wind (10 seconds) | Headset & Handset |
| Far-field male speech with silence gaps (6 seconds) | Headset & Handset |
| Far-field female speech with silence gaps (6 seconds) | Headset & Handset |
| Near-field male speech with silence gaps from HATS' mouth (6 seconds) | Headset & Handset |
| Near-field female speech with silence gaps from HATS' mouth (6 seconds) | Headset & Handset |
| Near-field male speech with silence gaps from handset receiver (6 seconds) | Handset |
| Near-field female speech with silence gaps from handset receiver (6 seconds) | Handset |
| Far-field tone sweep from 100-4000 Hz (87 seconds) | Headset & Handset |
| Near-field (from HATS' mouth) tone sweep from 100-4000 Hz (87 seconds) | Headset & Handset |

The tone sweeps mentioned in the final two rows of Table 3 each had a smoothly changing tone frequency that increased logarithmically over time. The speech mentioned in rows 4-9 of Table 3 consisted of two spoken sentences separated by 1.3 seconds of silence (i.e. quiet, dominated by microphone noise) that started approximately 3 seconds into the stimuli, and the speech was presented at typical far-field and near-field sound levels. There were also short periods of quiet at the start and end of the speech stimuli. The wind speeds were chosen to cover a relevant range where wind noise levels approached and/or exceed speech levels. The wind stimuli were generated from a wind machine.

As for the evaluations with hearing aids and cochlear implant devices set out in Table 1, the WND algorithms of the present invention and of the prior art were implemented in Matlab/Simulink, and used to process non-overlapping consecutive blocks of samples of each microphone recording resulting from the stimuli of Table 3. For headset and handset applications, the processing was performed at a sampling rate of 8 kHz as is typical for these devices. The output of each WND algorithm was again processed by an IIR filter (b=[0.004]; a=[1 −0.996]) to smooth out any noise-like changes in the WND algorithm output that may exist from one block to another, and hence give a more consistent output for a constant input stimulus.

Figure 18A:
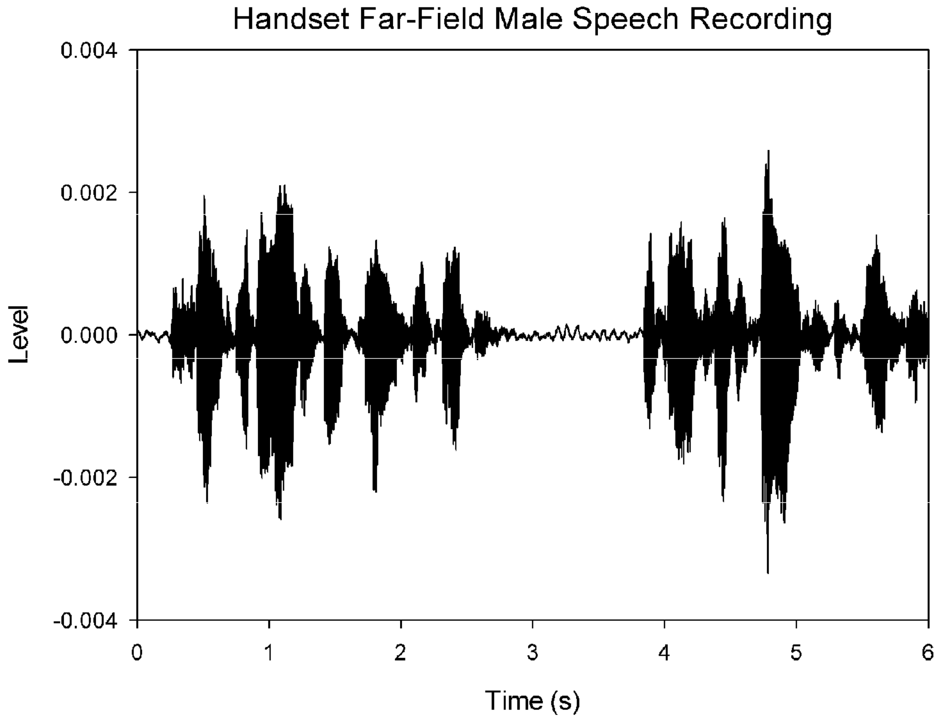
FIGS. 18*a* and 18*b* show examples of handset male and female speech stimuli used in the HATS experiments of FIGS. 19-22, the waveforms being recorded from a handset microphone.
Figure 18B:
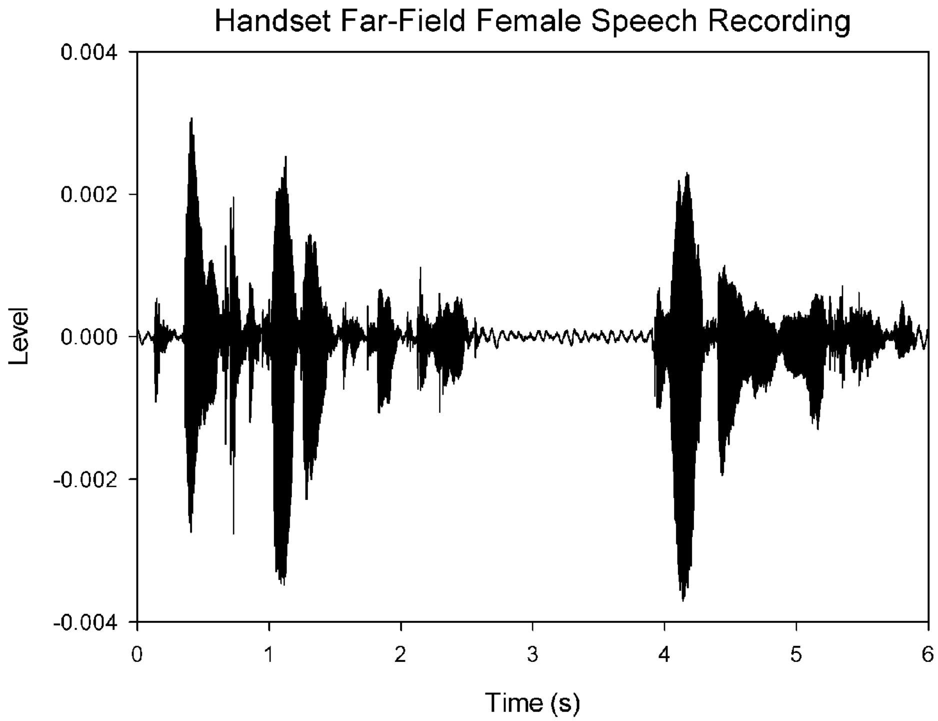

Examples of handset male and female speech recordings are shown in FIGS. 18*a* and 18*b* to more clearly indicate the speech gaps.

Figure 19A:
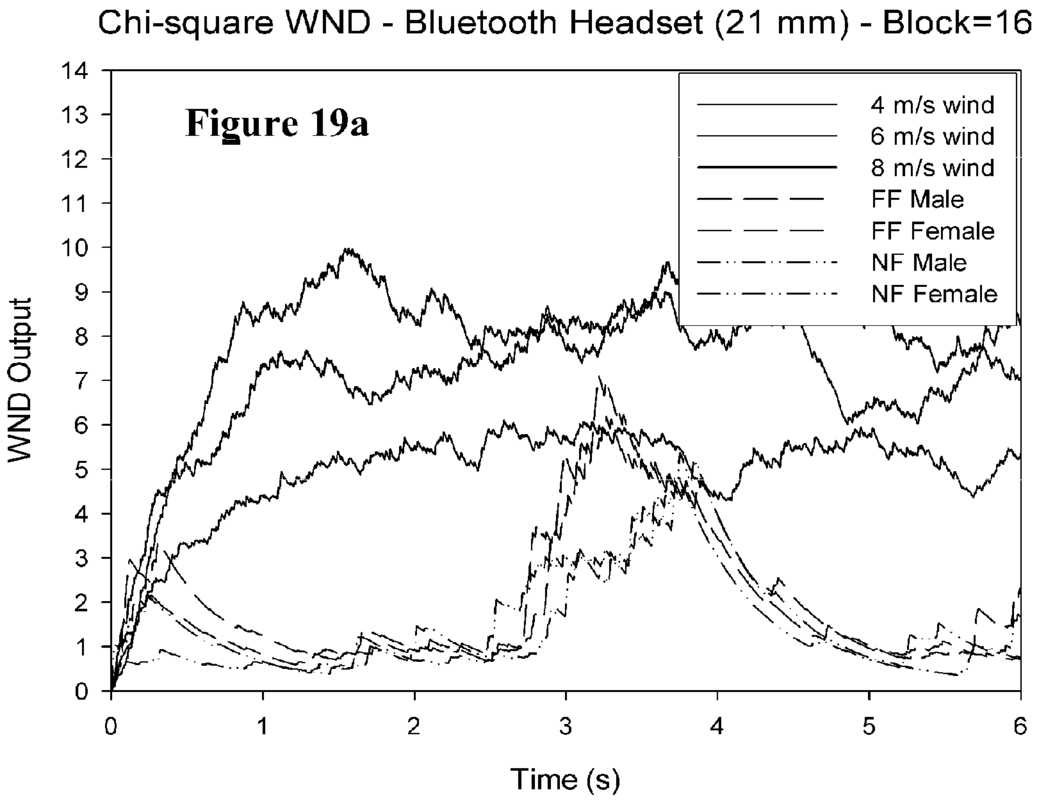
FIGS. 19*a*-19*e* show the outputs of the respective WND methods for Bluetooth headset recordings from a HATS, with a block size of 16 samples.

FIGS. 19*a*-19*e* show the outputs of the applied WND methods for Bluetooth headset recordings with a block size of 16 samples. The initial response starts from 0 in all cases due to the initialization of the smoothing IIR filter. As seen in FIG. 19*a* the Chi-squared WND method of the present invention clearly separates the wind noise from the speech. During the silence between the speech sentences, between about 3-4 seconds, the uncorrelated microphone noise results in wind-like values being returned by the Chi-squared WND method. However, since microphone noise is much lower in level (amplitude) than wind noise, a simple level threshold could be used to distinguish between microphone and wind noise.

Figure 19B:
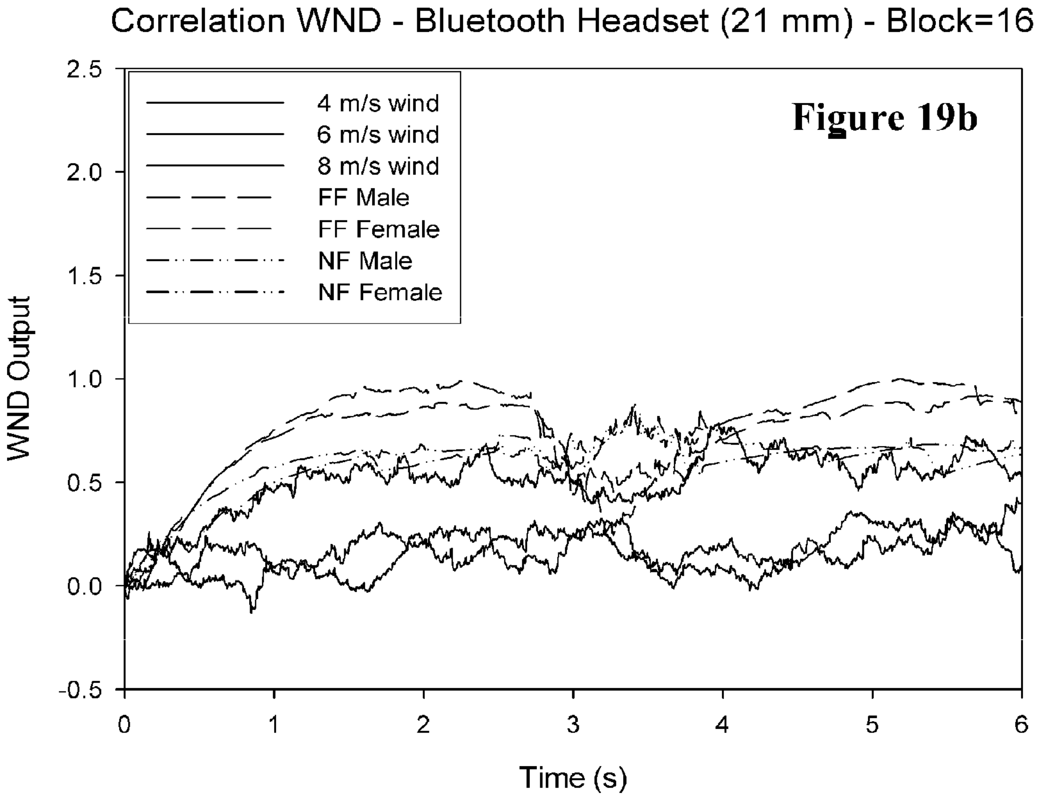
Figure 19C:
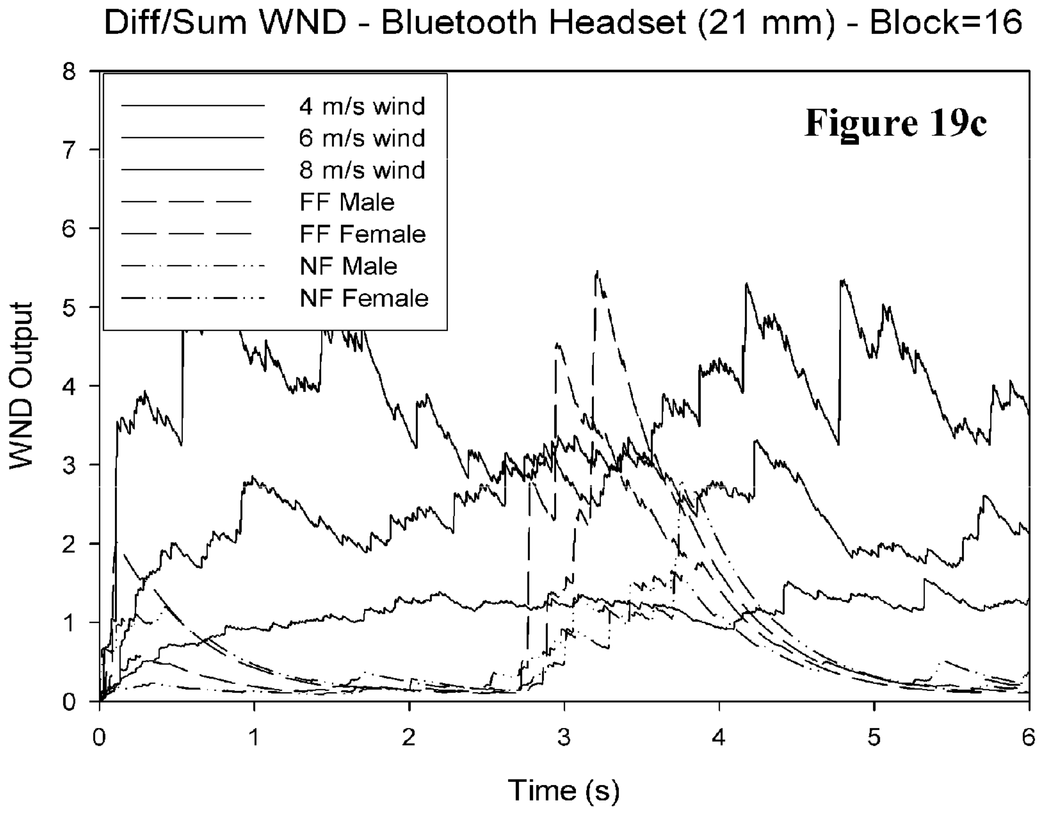
Figure 19D:
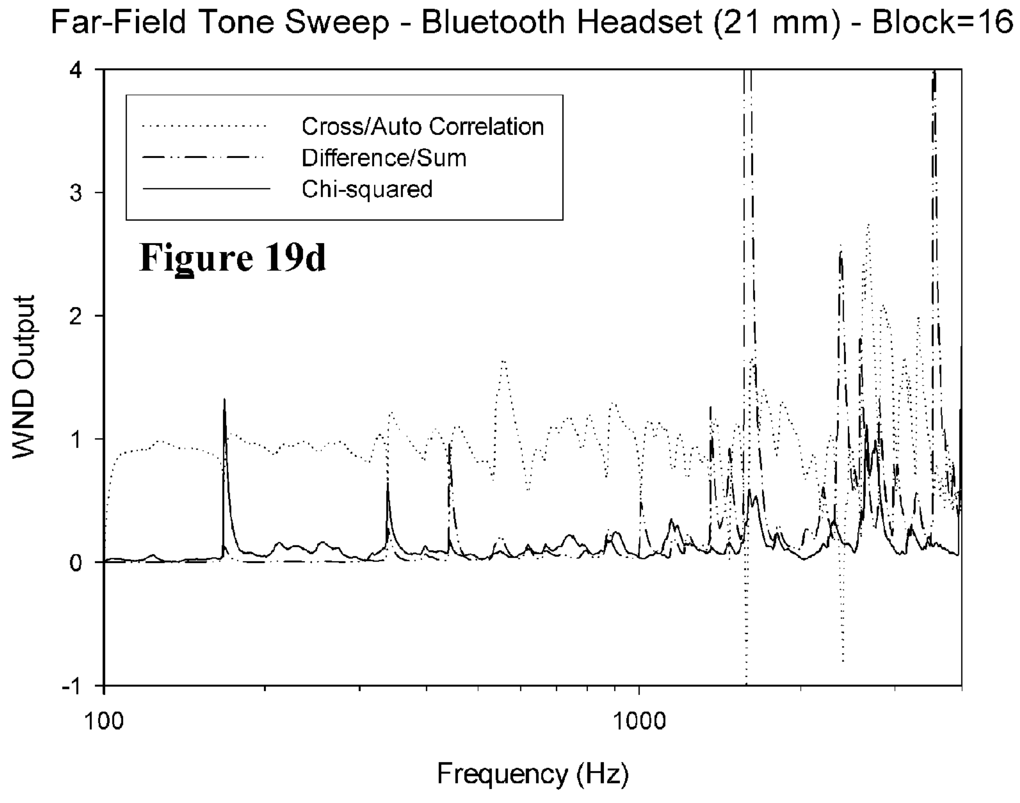
Figure 19E:
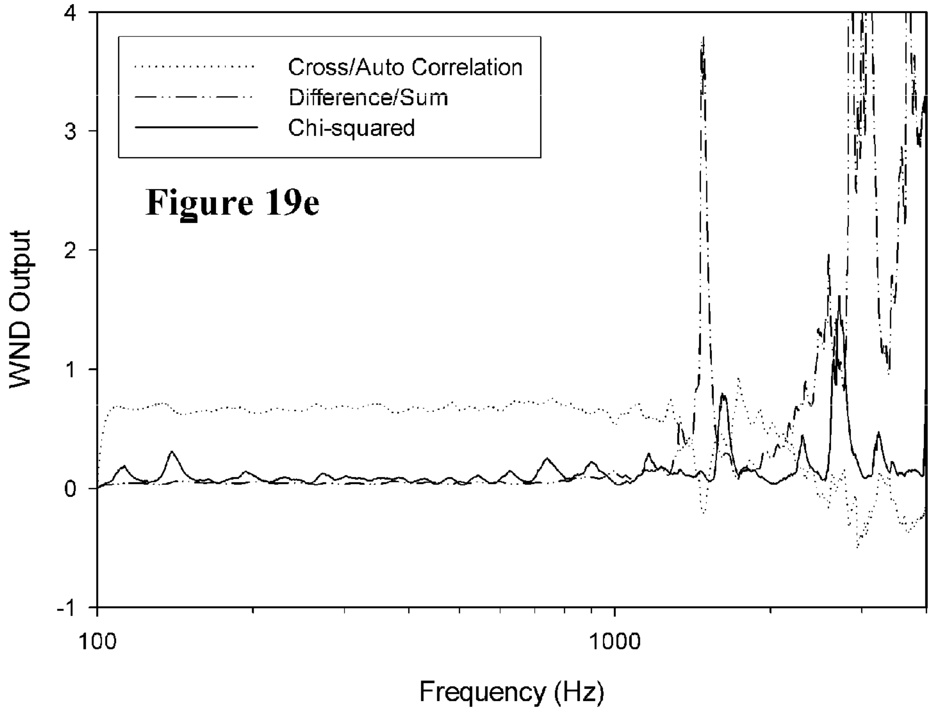

FIG. 19*b* reveals that the prior art correlation WND method can give similar values for speech and wind noise, and thus falsely detect speech as wind noise. FIG. 19*c* shows that the prior art Diff/Sum WND method gives values of approximately 0 for speech and 1 or more for wind noise and microphone noise. FIG. 19*d* shows output values in response to far field tone sweeps. The Chi-squared WND method output for far-field tones is less than 1.5 at all frequencies, which is similar to values for speech and clearly lower than values for wind noise. Thus, far-field tones are clearly separated from wind noise by the Chi squared method of the present invention. In contrast, the output of the correlation WND method for far-field tones can be around 1 (no wind) at some frequencies and around 0 (wind noise) at other frequencies. Thus, far-field tones can be falsely detected as wind noise by the correlation WND method. The output of the Diff/Sum WND method for far-field tones can be around 0 (no wind) at some frequencies and greater than 1 (wind noise) at other frequencies. Thus, far-field tones can be falsely detected as wind noise by the Diff/Sum WND method. FIG. 19*e* shows output values in response to near-field (mouth) tone sweeps. The Chi-squared WND method output for far-field tones is less than 2.0 at all frequencies, which is similar to values for speech and clearly lower than values for wind noise. Thus, near-field tones are clearly separated from wind noise by the Chi squared method of the present invention. In contrast, the output of the correlation WND method for near-field tones can be around 1 (no wind) at some frequencies and around 0 (wind noise) at other frequencies. Thus, near-field tones can be falsely detected as wind noise by the correlation WND method. The output of the Diff/Sum WND method for near-field tones can be around 0 (no wind) at some frequencies and greater than 1 (wind noise) at other frequencies. Thus, near-field tones can be falsely detected as wind noise by the Diff/Sum WND method.

Figure 20A:
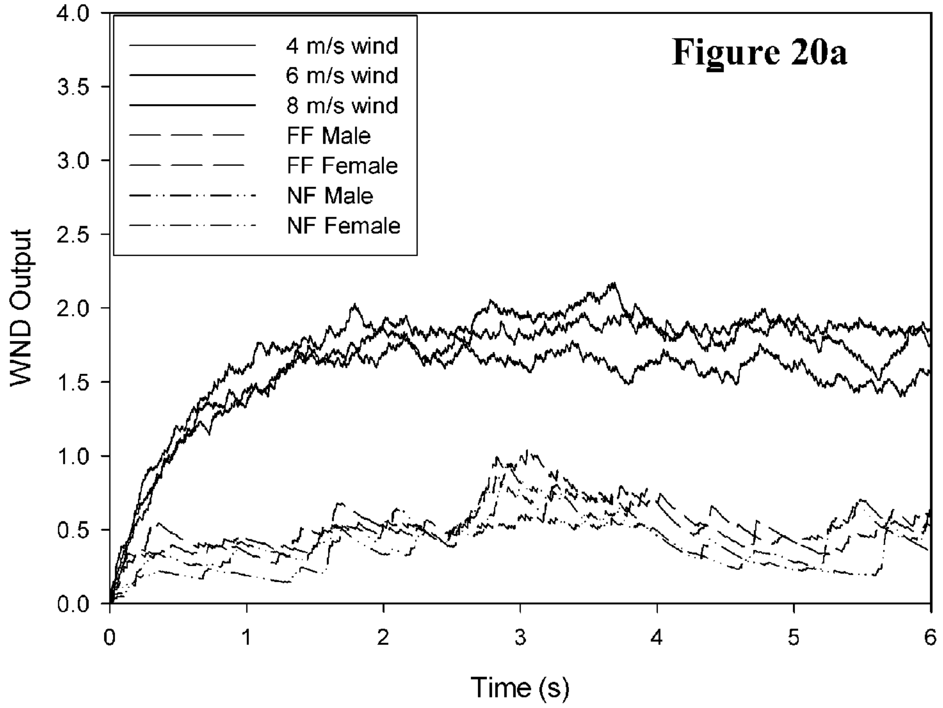
FIGS. 20*a*-20*c* show the outputs of the Chi-squared method for the recordings of FIG. 19 when applying a minimum Chi-squared method.
Figure 20B:
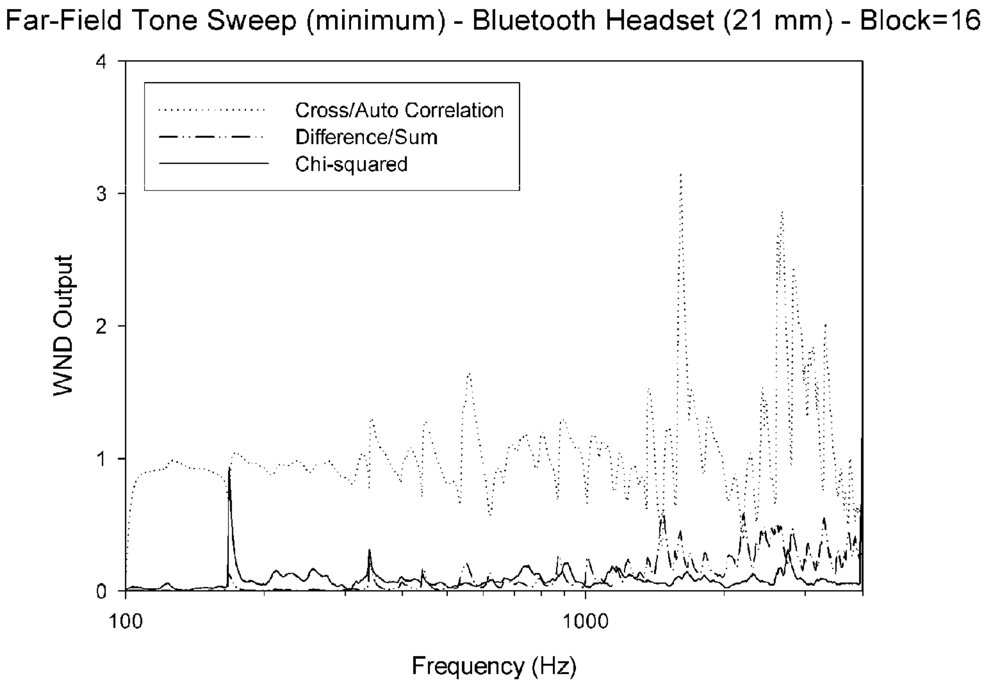
Figure 20C:
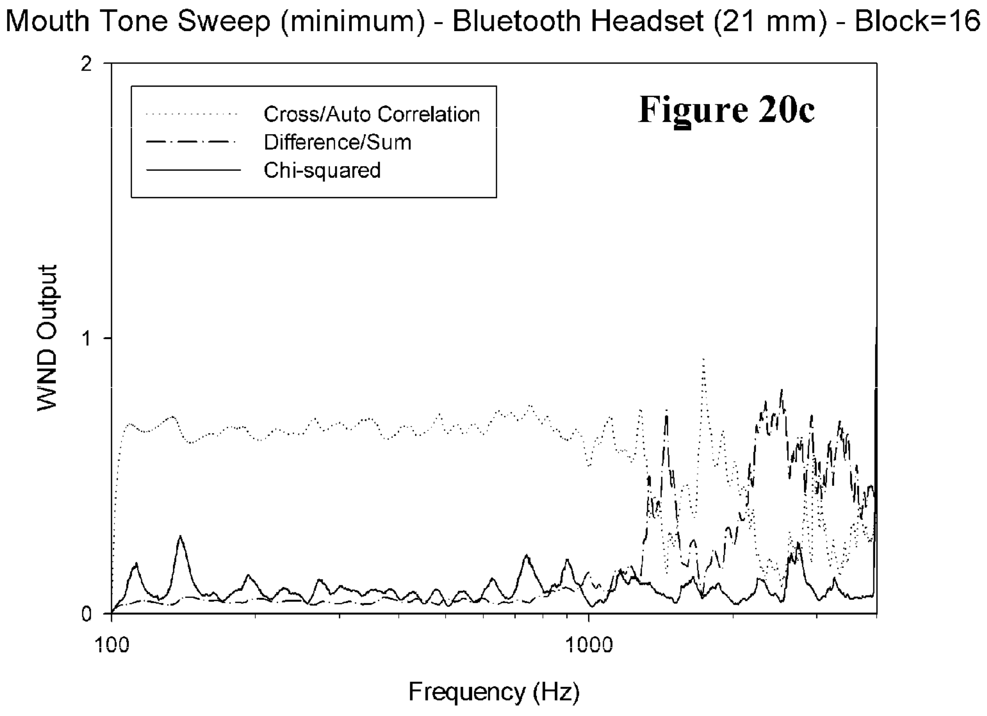

FIGS. 20*a*-20*c* show results when the Chi-squared calculation is repeated with one of the two microphone signals inverted in the manner described with reference to FIG. 10. The lower of the two Chi-squared values are output and passed through the smoothing filter. In simulations of tone sweeps, this made the Chi-squared WND method of the present invention more robust against tones. FIGS. 19*a*, 19*d* and 19*e* show that this may not be required with actual tone-sweep recordings, although FIGS. 20*a*-20*c* show that it can better separate the Chi-squared WND output for wind and microphone noise, which may be beneficial in reducing the need for an input level threshold to discriminate between these two types of noise. Actual tone sweep recordings include reverberation, microphone noise, and other effects that were not in simulations of pure/ideal sinusoidal stimuli, which may explain the differences between results with simulations and actual microphone signals.

FIG. 20*a* shows that by taking the minimum of the two Chi-squared values for each block, the output for microphone noise during the period 3-4 seconds is more similar to the output values for speech, and is clearly separated from the values for wind noise. Thus, a level threshold is not required to separate uncorrelated microphone noise from wind noise in this scenario if the minimum approach is applied.

As noted above and shown in FIG. 19*d*, the Chi-squared WND values output in response to a far field tone sweep were low enough to discriminate the tone from wind, without taking the minimum of the two Chi-squared values. Nevertheless, FIG. 20*b* shows that the Chi-squared WND values for far-field tones can be reduced (improved) by taking the minimum values.

As noted above and shown in FIG. 19*e*, the Chi-squared WND values output in response to near-field (mouth) tones were low enough to discriminate the near-field tones from wind, without taking the minimum of the two Chi-squared values. Nevertheless FIG. 20*c* shows that the Chi-squared WND values for near-field (mouth) tones are also reduced (improved) by taking the minimum values.

Figure 21A:
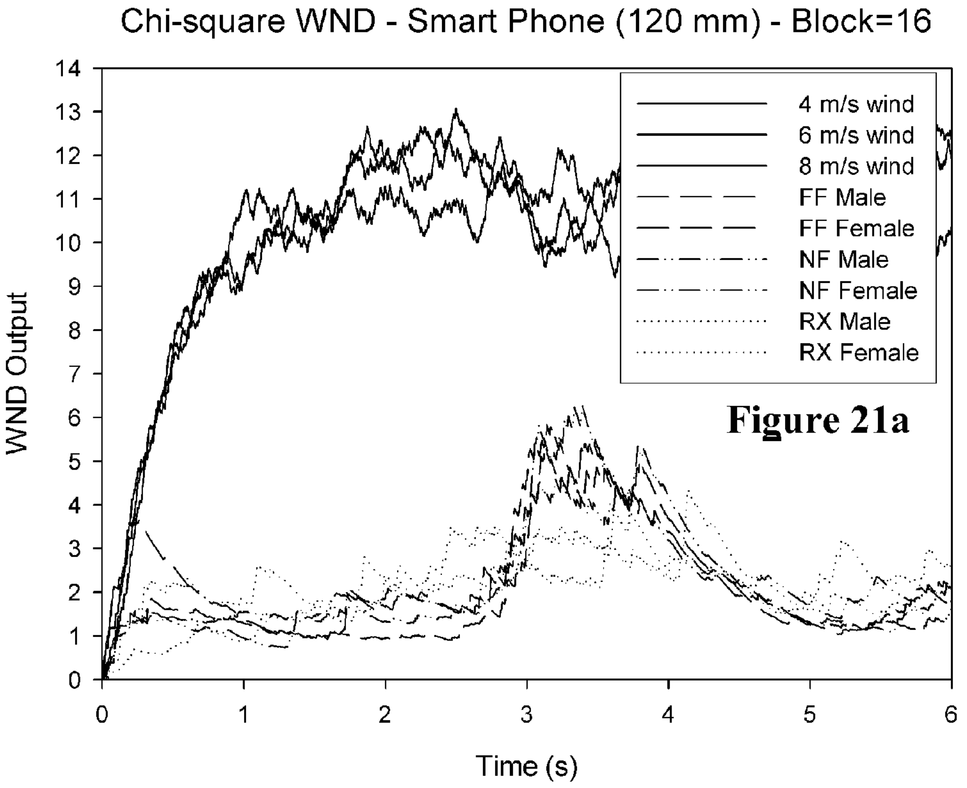
FIGS. 21*a* to 21*e* show the outputs of the respective WND methods for smart phone recordings from a HATS, with a block size of 16 samples.

FIGS. 21*a* to 21*e* show the outputs of the different WND methods for a smart phone with a block size of 16 samples. As before, the initial response starts from 0 in all cases due to the initialization of the smoothing IIR filter. FIG. 21*a* shows that the Chi-squared WND method of the present invention clearly separates the wind noise from the speech and the microphone noise during the speech gaps around 3-4 seconds, so that no level threshold is required to assist to distinguish wind noise from microphone noise. The greater average Chi-squared values with the handset compared with the headset are probably due to the greater microphone spacing, which made the locally generated wind noise less similar between microphones.

Figure 21B:
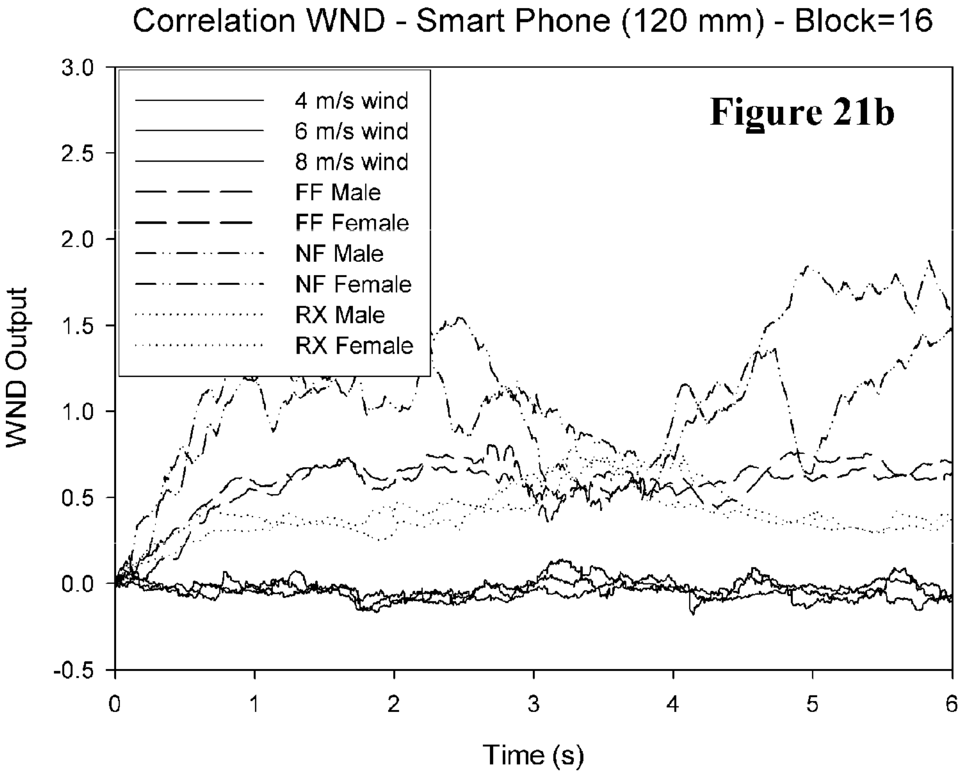
Figure 21C:
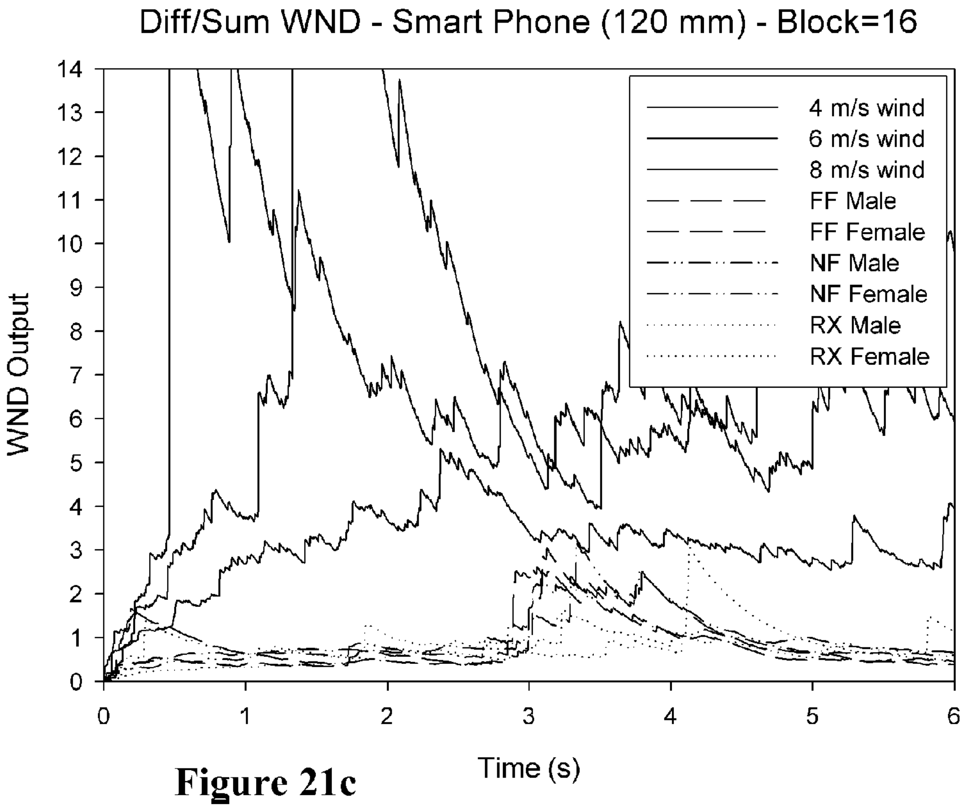
Figure 21D:
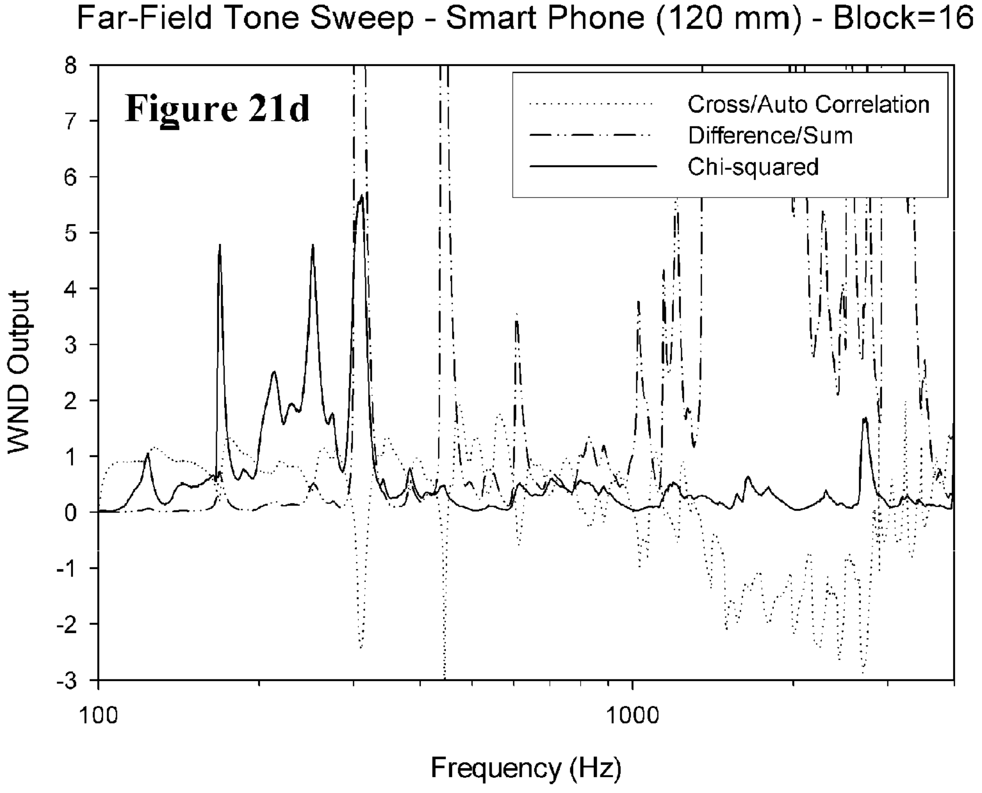

FIG. 21*b* shows that the correlation WND method only narrowly separates wind noise from non-wind stimuli. FIG. 21*c* shows that the Diff/Sum WND method has separated wind noise from speech, but not wind noise from microphone noise in the speech gaps around 3-4 seconds. FIG. 21 *d* shows that the Chi-squared WND method of the present invention gives output values for far-field tones which are similar to values for other non-wind stimuli, and which are well below typical values for wind noise (being values around 9-12 as shown in FIG. 21*a*). Thus, far-field tones are clearly separated from wind noise by the Chi-squared WND method of the present invention. In contrast, the correlation WND method's output for far-field tones can be the same as values for wind noise at some frequencies. Thus, far-field tones can be falsely detected as wind noise by the correlation WND method. The Diff/Sum WND method's output for far-field tones can be the same as values for wind noise at some frequencies. Thus, far-field tones can be falsely detected as wind noise by the diff/sum WND method.

Figure 21E:
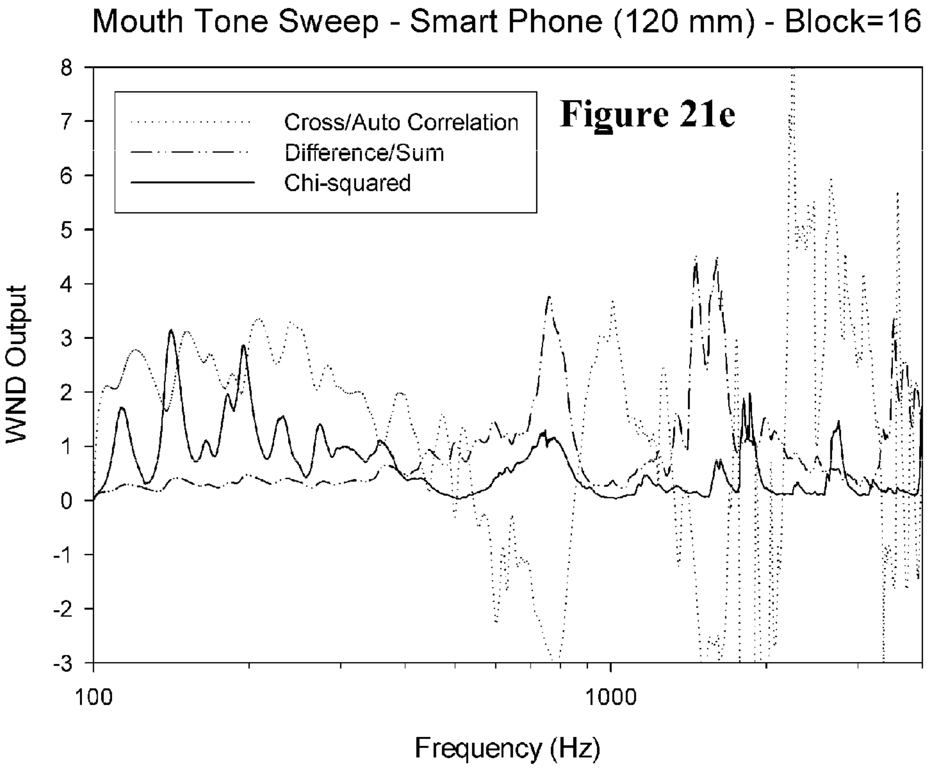

FIG. 21*e* shows that the Chi-squared WND method's output for near-field (mouth generated) tones is similar to values for other non-wind stimuli, and is well below typical values for wind noise. Thus, near-field (mouth generated) tones are clearly separated from wind noise. The correlation WND method's output for near-field (mouth generated) tones can be the same as values for wind noise at some frequencies. Thus, near-field (mouth generated) tones can be falsely detected as wind noise by the correlation WND method. The Diff/Sum WND method's output for near-field (mouth generated) tones can be the same as values for wind noise at some frequencies. Thus, near-field (mouth generated) tones can be falsely detected as wind noise by the diff/sum WND method.

Figure 22A:
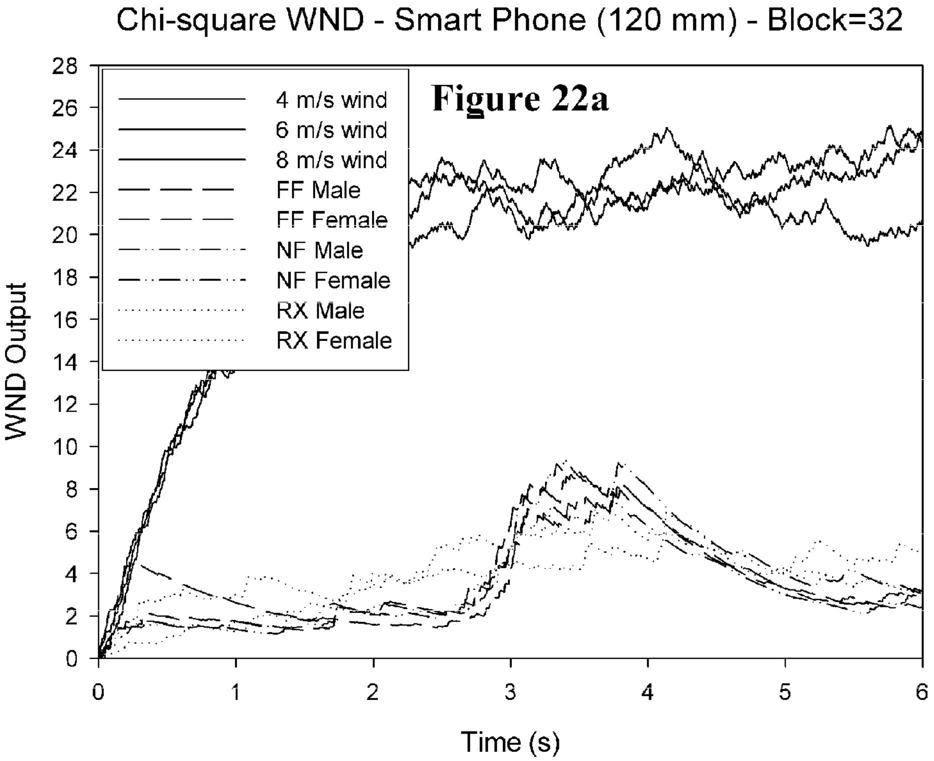
FIGS. 22*a* to 22*e* show the outputs of the respective WND methods for smart phone recordings from a HATS, with a block size of 32 samples.
Figure 22B:
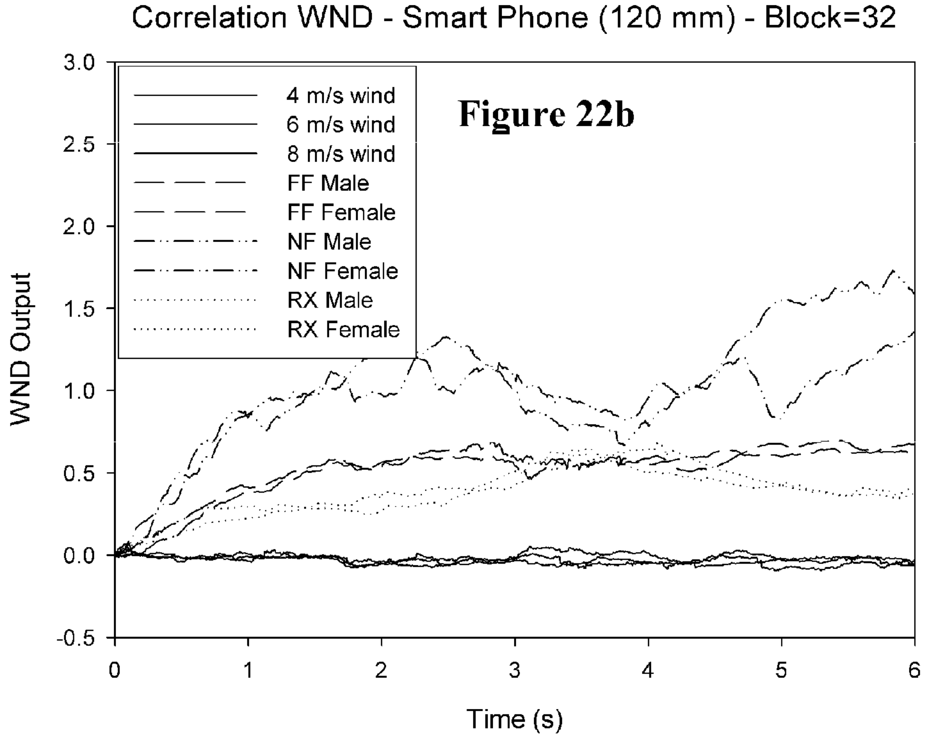
Figure 22C:
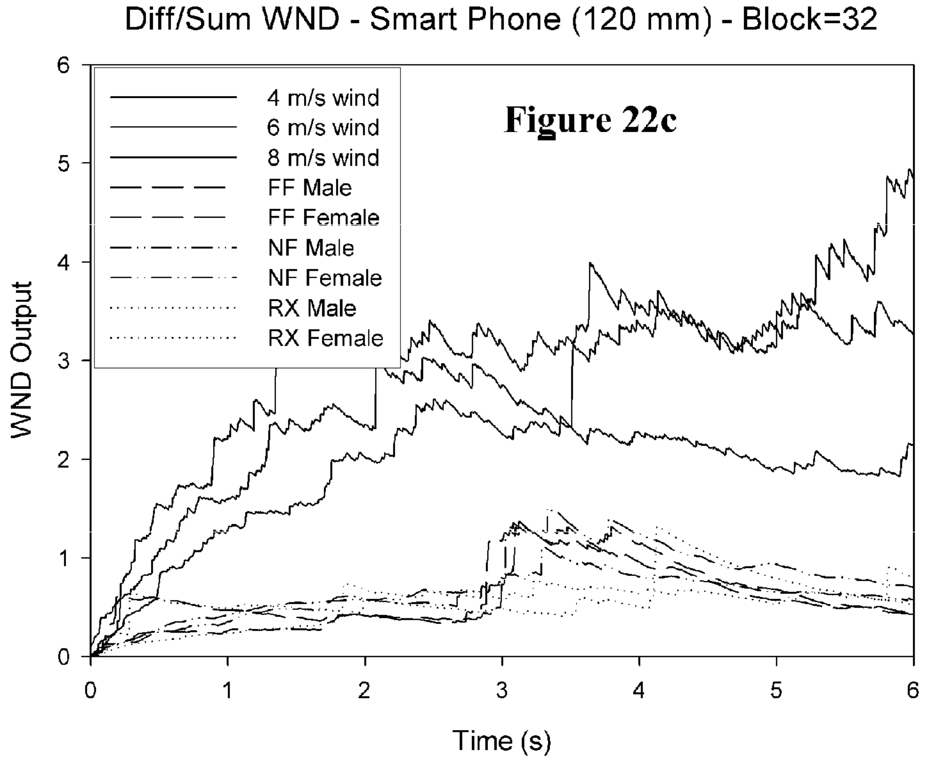

Compared with a smart phone handset using a block size of 16 samples (as shown in FIGS. 21*a-e*), a block size of 32 samples makes the Chi-squared WND method of the present invention even more robust at differentiating wind noise from far-field and near-field tones. This is shown in FIGS. 22*a-e*. In FIG. 22*a* the Chi-squared WND method clearly differentiates the wind noise inputs from the other stimuli presented. FIGS. 22*b* and 22*c* show that the correlation WND method and diff/sum WND method also experience improvement with the larger block size, but that the discrimination of wind noise from other stimuli is less definitive than for the Chi-squared WND method of the present invention.

Figure 22D:
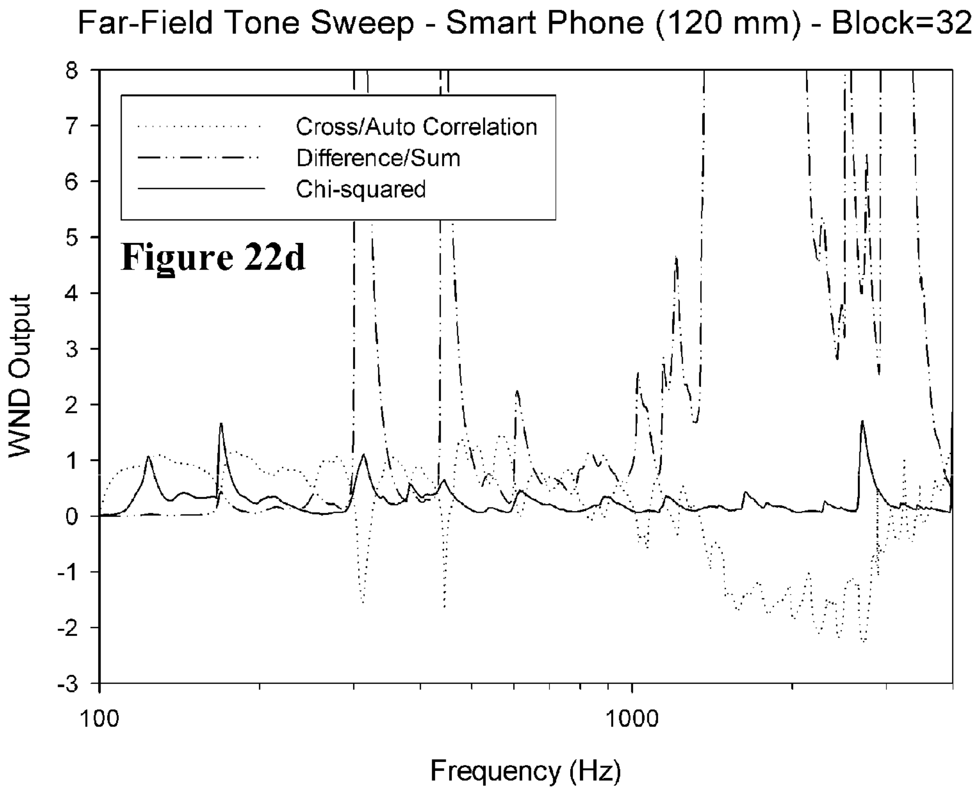
Figure 22E:
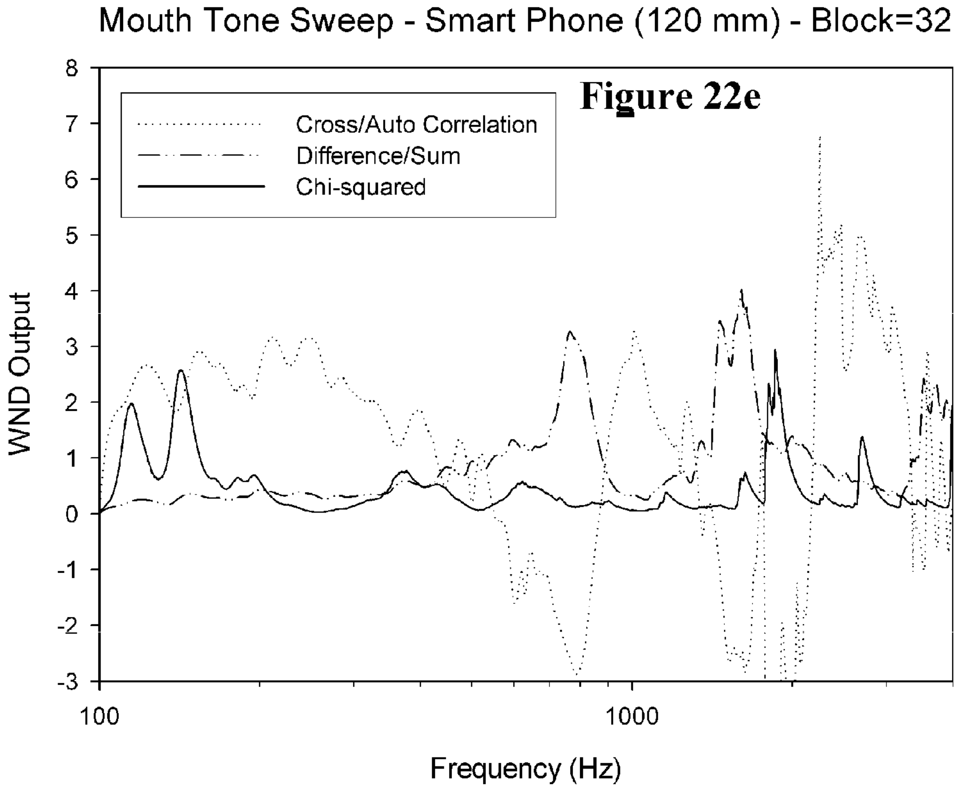

FIG. 22*d* shows that the Chi-squared WND output for far-field tones is well below the values for wind noise with a block size of 32 samples, whereas the correlation WND method and the diff/sum WND method will fail to correctly discriminate between far-field tones and wind noise at some frequencies. FIG. 22*e* shows that the Chi-squared WND output for near-field tones (from the mouth) is well below the values for wind noise with a block size of 32 samples, whereas the correlation WND method and the diff/sum WND method will fail to correctly discriminate between near-field tones and wind noise at some frequencies.

Figure 23A:
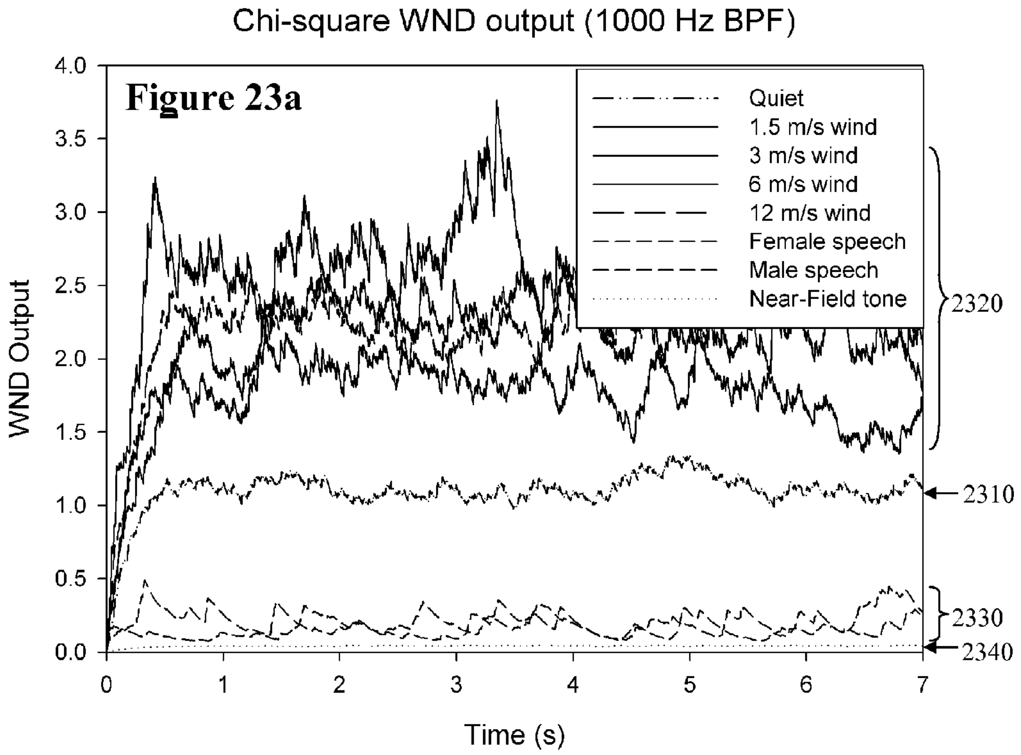
FIGS. 23*a* to 23*c* show the outputs of the Chi-squared methods for pre-recorded input signals processed by 1000 Hz and 5000 Hz time-domain, sub-band filters.
Figure 23B:
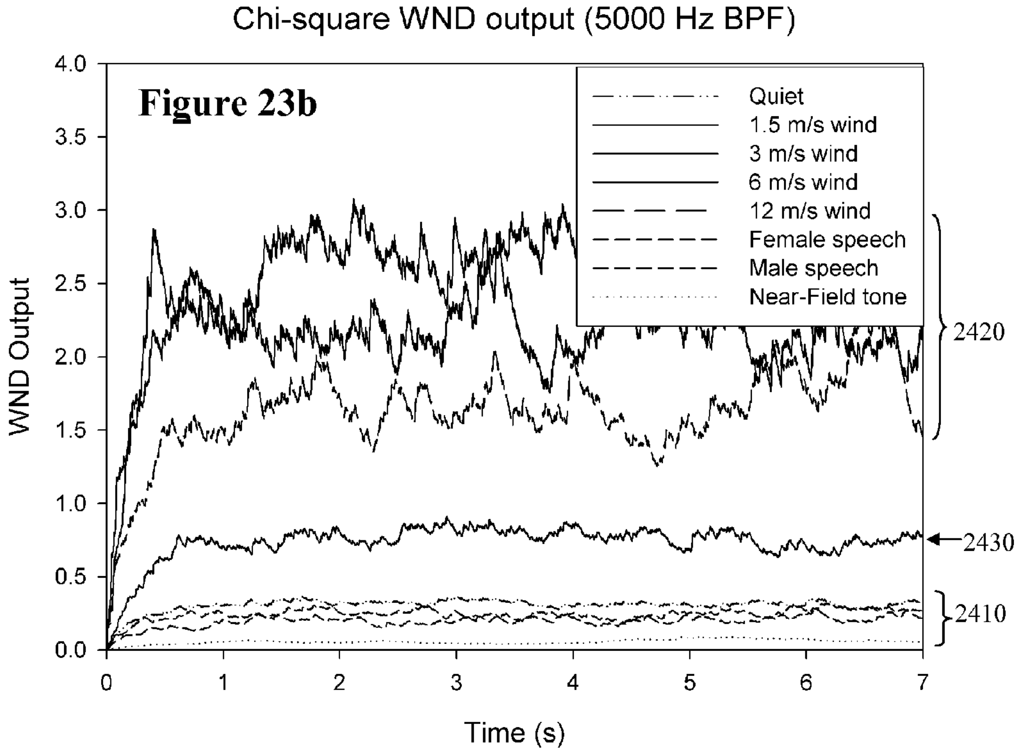
Figure 23C:
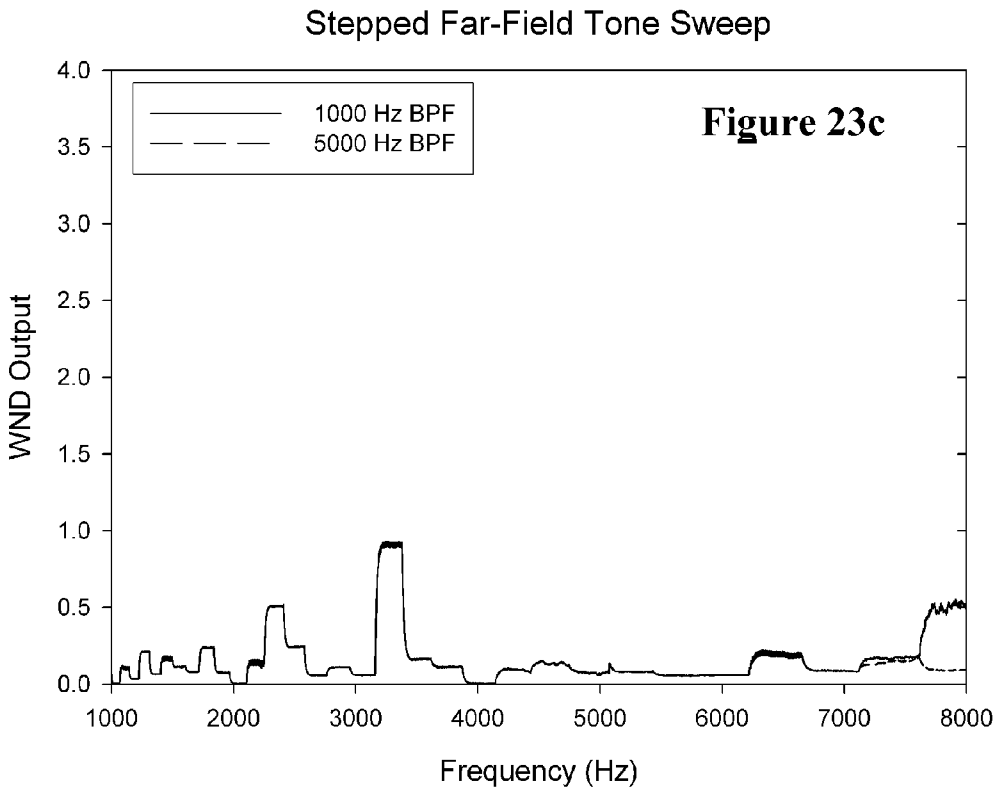

FIGS. 23*a-c* illustrate wind noise detector results obtained by a sub-band, time-domain implementation of the Chi-squared WND shown in FIG. 2. The performance of this sub-band time domain implementation was evaluated in response to the stimuli set out in Table 1 in the preceding. Second-order, bi-quadratic, IIR, one-octave, band-pass filters were constructed in Matlab/Simulink and filtered the pre-recorded microphone signals into sub-bands, and the sub-band microphone signals were then processed by the Chi-squared WND. These exemplary IIR filters were chosen because of their ease and efficiency of implementation in typical DSP processing devices, however different orders and types of filter with different cut-off frequencies may be used as appropriate for this and other applications. As for the full-band implementation, the output of the WND algorithm was processed by an IIR filter (b=[0.004]; a=[1 −0.996], it being noted that other filter types and coefficients could be used) to smooth out any jitter-like changes in the WND algorithm output that may exist from one block to another, and hence give a more consistent output for a constant input stimulus.

FIG. 23*a* shows the smoothed Chi-squared WND output for the wind, speech, microphone noise (quiet), and 1 kHz near-field tone stimuli processed by a one-octave, band-pass, second-order, IIR filter centred on 1 kHz. The near-field tone is at this band-pass filter's centre frequency. There is clear separation between the smoothed WND output for the wind noise (collectively, 2320) and the smoothed output for speech stimuli (collectively, 2330). The output 2310 for the microphone noise lies between the outputs for wind and speech. The peaks for the speech stimuli are due to gaps between phonemes where the microphone noise dominated. As previously described, the use of an SPL threshold could be used if there was a need to more clearly distinguish between wind noise and microphone noise, and this would also reduce the height of the peaks between phonemes for the speech stimuli. The smoothed WND output 2340 for the near-field tone at this sub-band's centre frequency is lower than for speech and is almost zero, thereby correctly indicating no wind.

FIG. 23*b* shows the smoothed Chi-squared WND output for the wind, speech, microphone noise, and 1 kHz near-field tone stimuli processed by a one-octave, band-pass, second-order, IIR filter centred on 5 kHz. Significant amounts of wind noise can exist at such high frequencies, and as previously demonstrated, other WND methods may not reliably discriminate between wind noise and other sounds as such high frequencies. The smoothed Chi-squared WND outputs for speech, microphone noise (quiet), and the 1 kHz near-field tone (collectively, 2410) are all well below 0.5. The smoothed WND outputs for wind from 3-12 m/s (collectively, 2420) are all above approximately 1.0. For the 5 kHz band assessed in this case, the smoothed WND output 2430 for wind at 1.5 m/s lies between 0.5 and 1.0, and this is because wind noise is concentrated in the lower frequencies at this wind speed. Thus, the Chi-squared WND has correctly reduced its output for low-speed wind that results in little wind noise around 5 kHz, and a Chi-squared threshold of approximately 1.0 could be used to not detect 1.5 m/s wind in the 5 kHz band. A higher-order, band-pass filter with a steeper low-frequency roll-off would detect less lower-frequency wind noise, and result in an even lower smoothed WND output for 1.5 m/s wind.

FIG. 23*c* shows the smoothed Chi-squared WND output for the stepped tone sweep processed by the same one-octave, band-pass, second-order, IIR filters centred on 1 kHz and 5 kHz used to produce the results of FIGS. 23*a* and 23*b*. In both cases, the smoothed Chi-squared WND output is below 1.0 and very similar to the smoothed WND output for the full-band implementation of the Chi-squared WND seen in FIG. 7, which confirms the robustness of these exemplary sub-band implementations of the Chi-squared WND.

FIGS. 24*a-e* show data for stimuli that were processed by a FFT in the frequency domain before processing by the Chi-squared WND. The FFT implementation of the Chi-squared WND shown in FIG. 3 was evaluated with the same pre-recorded microphone signals and methods as the full-band, time-domain version shown in FIG. 1. These stimuli are listed in Table 1 in the preceding.

The operation of the Chi-squared WND in the frequency domain was evaluated in Matlab/Simulink with the pre-recorded microphone signals, which were sampled at a rate of 16 kHz. For each microphone, overlapping blocks of 64 samples were processed by a 64-point Hanning window and a 64-point Fast Fourier Transform (FFT). A FFT was computed every 32 samples, or 2 milliseconds, (i.e. 50% overlap between FFT frames), and the complex FFT data for each bin were converted to magnitude values, and the magnitude values were converted to dB units. While this FFT processing may be exemplary in DSP hearing aid applications, this is not intended to exclude other combinations of sampling rate, window, FFT size, and processing of the raw complex FFT output data into other values or units.

After each pair of FFTs was computed (i.e. one for each of the two microphones), the dB values were stored in buffers of the most recent 16 values (one buffer for each combination of microphone and FFT bin as shown in FIG. 3). Then for each FFT bin, the mean of the values in the corresponding first and second microphone buffers were calculated and used as the first and second comparison thresholds, respectively. However, if a dB value in the buffer was below its corresponding input level threshold, the comparison thresholds for both microphones were set so that they were above all of the dB values in the corresponding buffers. This resulted in a Chi-squared value of 0. The input level thresholds were set to be 5 dB above the maximum microphone noise level for each FFT bin, and this was required to avoid microphone noise from being incorrectly detected as wind noise by this FFT implementation of the Chi-squared WND. Higher input level thresholds may be used to ensure that wind that is inaudible or unobtrusive to the user is not detected.

The data in the buffers were then compared to the corresponding comparison thresholds in order to count the number of positive and negative values with respect to the comparison thresholds. Values that were within 0.5 dB of the corresponding comparison threshold were treated as being equal to that comparison threshold, and hence counted as a positive value. This improved how well this FFT implementation of the Chi-squared WND handled constant pure-tone inputs, which may toggle either side of the comparison threshold by a very small extent, such as less than 0.1 dB, in a pattern that may not be the same across microphones, and lead to the incorrect detection of a tone as wind noise. The positive and negative value counts were then processed as previously described to calculate the Chi-squared WND output, which was processed by a previously described IIR smoothing filter (b=[0.004]; a=[1 −0.996]).

Figure 24A:
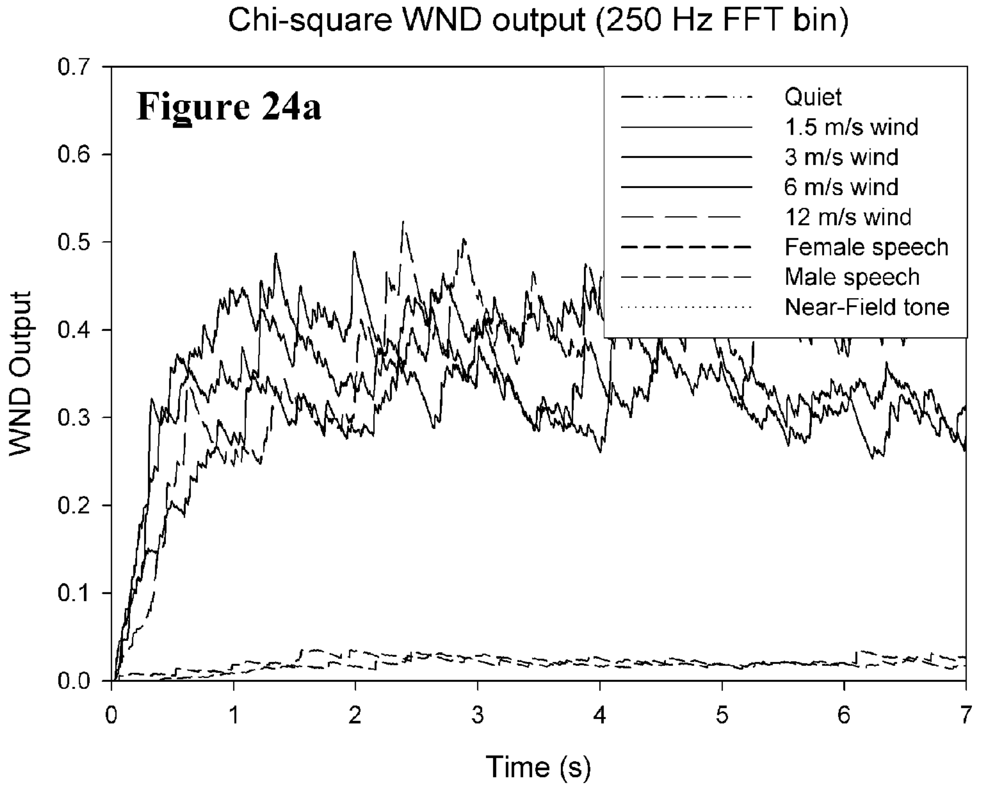

FIG. 24*a* shows the smoothed Chi-squared WND output for the wind, speech, microphone noise (quiet), and 1 kHz near-field tone stimuli for the 250 Hz FFT bin. The output for the near-field tone and microphone noise is zero, and there is clear separation between the values for speech and wind noise, indicating correct detection of wind noise at 250 Hz. A suitable wind detection threshold may lie between approximately 0.1 and 0.2. Overall, the smoothed Chi-squared output values for wind noise and speech are lower than for the time-domain implementations of the Chi-squared WND.

Figure 24B:
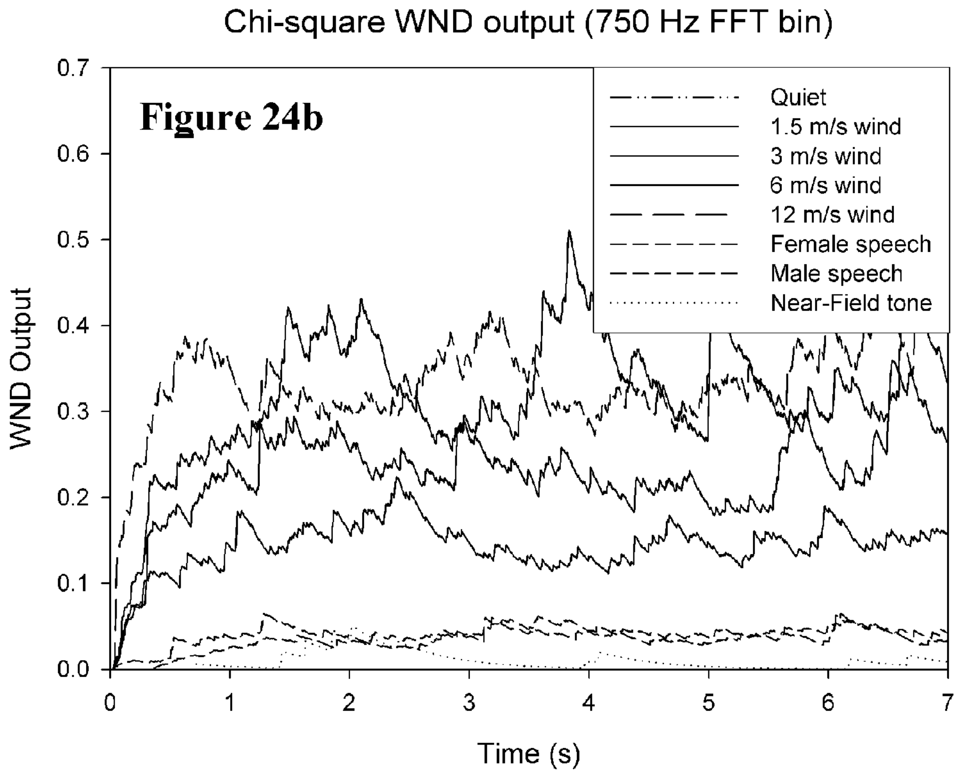

FIG. 24*b* shows the smoothed Chi-squared WND output for the 750 Hz FFT bin. The smoothed Chi-squared WND output is clearly less than 0.1 for speech, and is zero for the microphone noise and near zero for the 1 kHz near-field tone. The smoothed values for 1.5 m/s wind are lowest and vary between approximately 0.1 and 0.2, while the smoothed values for 3 m/s wind are slightly higher and vary around 0.2. This is correct behaviour, since the level of the 1.5 m/s wind noise is only approximately 12 dB above the microphone noise in the 750 Hz FFT bin and may not be audible, and optionally should not be detected. The level of the 3 m/s wind noise is also reduced (but to a lesser extent) compared with the 250 Hz FFT bin, and with a lesser reduction in the smoothed Chi-squared values that still tend to remain above 0.2 depending on the consistency of the wind noise. The levels of the 6 and 12 m/s wind noise are well clear of the microphone noise, and have clearly higher smoothed Chi-squared values that would appropriately be categorized as wind noise.

Figure 24C:
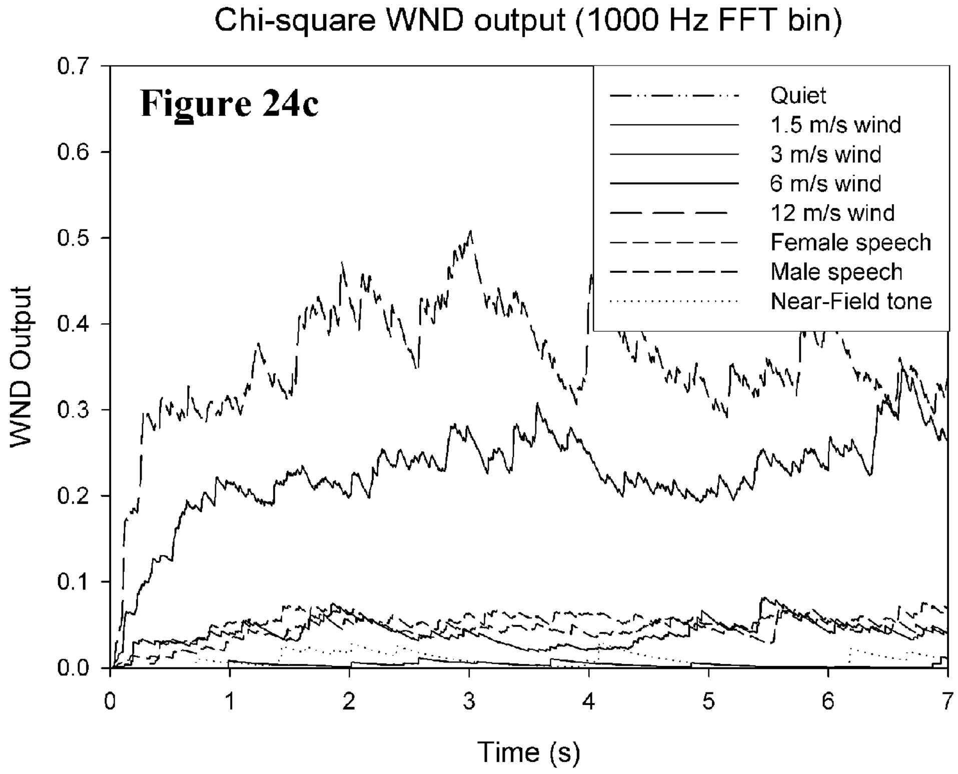

FIG. 24*c* shows the smoothed Chi-squared WND output for the 1000 Hz FFT bin. The near-field tone is at this band-pass filter's centre frequency. The smoothed Chi-squared WND output is clearly less than 0.1 for speech, and is zero for the microphone noise and near zero for the 1 kHz near-field tone. The smoothed values for 1.5 and 3 m/s wind noise are close to zero because the wind noise levels are close to the microphone noise level in this FFT bin. Thus, the Chi-squared WND has correctly not detected wind noise at wind speeds that do not result in significant amounts of wind noise at 1 kHz. The smoothed Chi-squared values for 6 and 12 m/s wind are clearly higher than those for speech, since the wind noise has significant energy at 1 kHz at these wind speeds, so wind noise can be correctly detected at these wind speeds in the 1 kHz FFT bin.

Figure 24D:
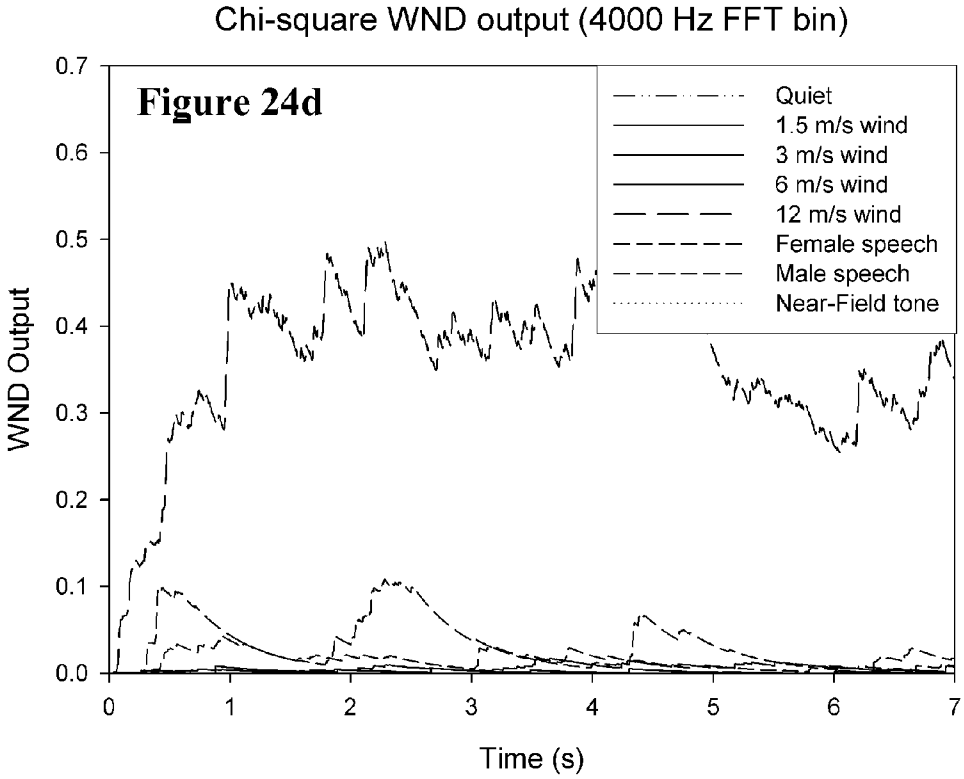

FIG. 24*d* shows the smoothed Chi-squared WND output for the 4000 Hz FFT bin. At this frequency, only the 12 m/s wind noise has significant energy and can be correctly classified as wind from the smoothed Chi-squared WND output. The smoothed output for all other stimuli is less than 0.1, which is appropriate for the lower wind speeds and non-wind stimuli.

Figure 24E:
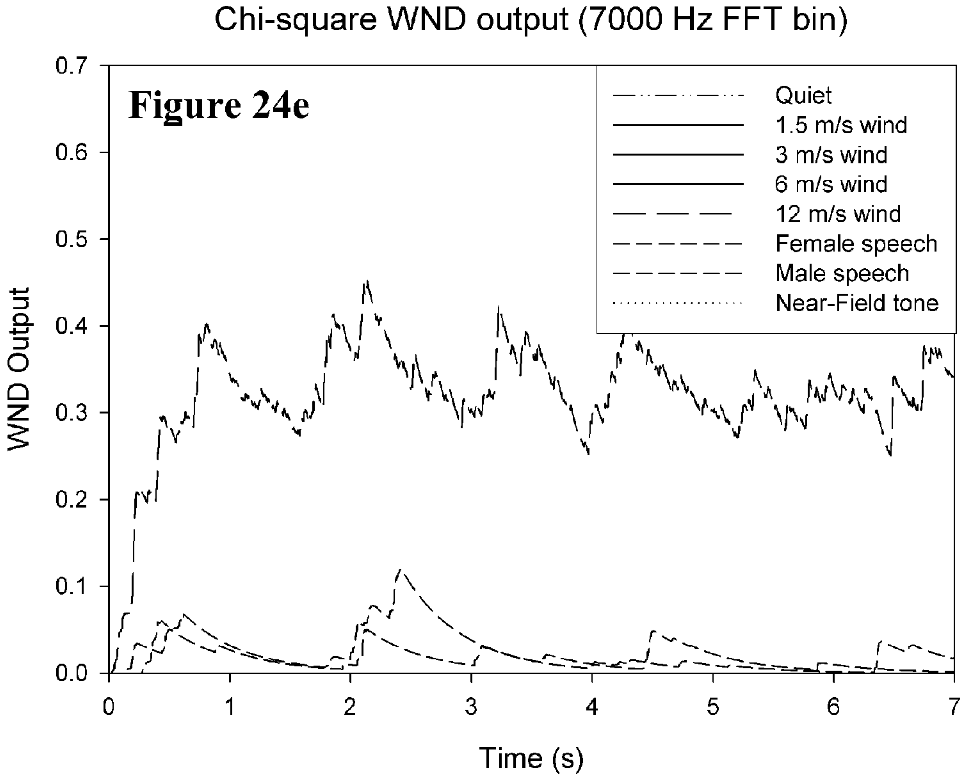

FIG. 24*e* shows the smoothed Chi-squared WND output for the 7000 Hz FFT bin. At this frequency, only the 12 m/s wind noise has significant energy and can be correctly classified as wind from the smoothed Chi-squared WND output. The smoothed outputs for all other stimuli tend to be less than 0.1, which is appropriate for the lower wind speeds and non-wind stimuli. Thus, this exemplary FFT implementation of the Chi-squared WND can correctly detect wind noise where it exists at very high frequencies, and discriminate between wind noise and non-wind sounds. Compared with the sub-band time-domain implementation, the FFT implementation of the Chi-squared WND operates on narrower frequency bands and processes data that covers a larger period of time but with reduced time resolution due to the conversion of blocks of samples into RMS input level estimates. These differences explain the differences shown between the Chi-squared WND output for these implementations.

Figure 24F:
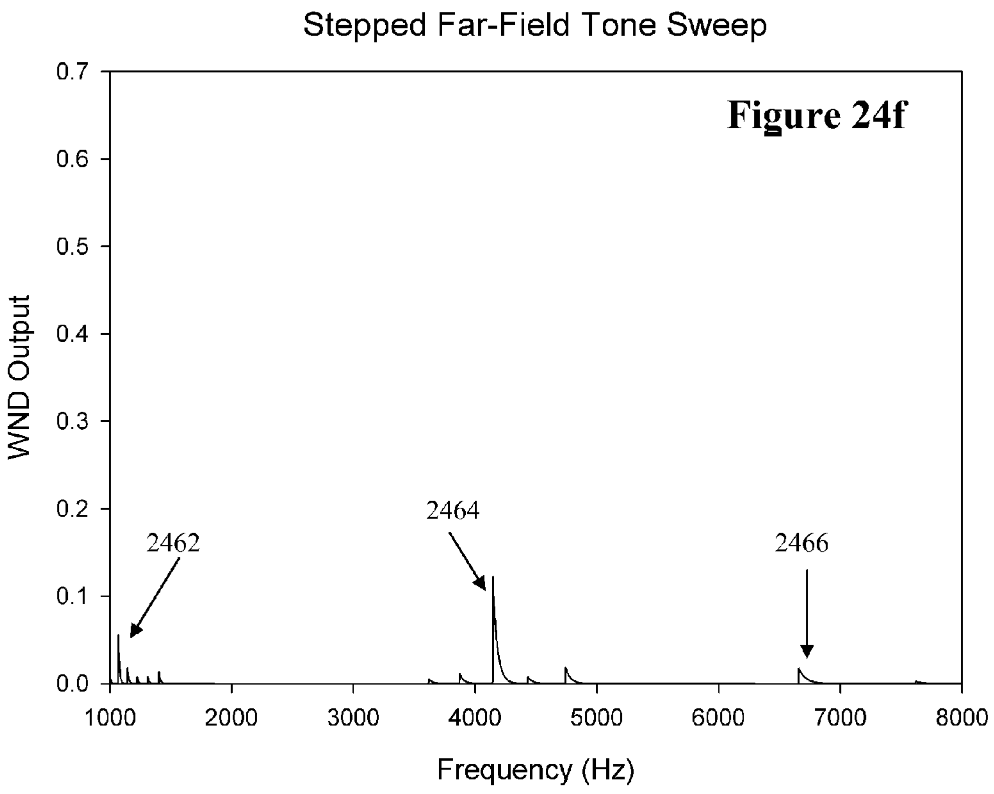
FIG. 24*f* shows the outputs of the Chi-squared methods for a pre-recorded input stepped tone sweep signal processed by 1000, 4000 and 7000 Hz FFT bins.

FIG. 24*f* shows the smoothed Chi-squared WND outputs 2462, 2464, 2466 for the far-field stepped tone sweep for the 1000 Hz, 4000 Hz, and 7000 Hz FFT bins, respectively. The smoothed output is generally zero, with spikes that are generally less than 0.1 and correspond to step changes in tone frequency that resulted in steep transients. The spikes tend to be for frequencies near each FFT bin's centre frequency. This confirms the robustness of this FFT implementation of the Chi-squared WND against falsely detecting non-wind stimuli as wind noise.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of processing digitized microphone signal data for detecting wind noise, the method comprising:

obtaining from a first microphone a first set of signal samples;

obtaining from a second microphone a second set of signal samples arising substantially contemporaneously with the first set;

determining a first number of samples in the first set which are greater than a first predefined comparison threshold, and determining a second number of samples in the first set which are less than the first predefined comparison threshold;

determining a third number of samples in the second set which are greater than a second predefined comparison threshold, and determining a fourth number of samples in the second set which are less than the second predefined comparison threshold; and determining whether the first number and second number differ from the third number and fourth number to an extent which exceeds a predefined detection threshold, and if so outputting an indication that wind noise is present.

2. The method according to claim 1 wherein the first predefined comparison threshold is the same as the second predefined comparison threshold.

3. The method according to claim 1 wherein the first predefined comparison threshold is zero.

4. The method according to claim 1 wherein the second predefined comparison threshold is zero.

5. The method according to claim 1 wherein the first predefined comparison threshold is the mean of selected past signal samples.

6. The method according to claim 1 wherein the second predefined comparison threshold is the mean of selected past signal samples.

7. The method according to claim 1 wherein the step of determining whether the number of positive and negative samples in the first set differ from the second set to an extent which exceeds a predefined detection threshold is performed by applying a Chi-squared test.

8. The method according to claim 7 wherein, if the Chi-squared calculation returns a value below the predefined detection threshold then an indication of an absence of wind noise is output, and if the Chi-squared calculation returns a value greater than the detection threshold an indication of the presence of wind noise is output.

9. The method according to claim 8 wherein for a sample block size of 16 and microphone spacing of 12 mm the detection threshold is in the range of 0.5 to about 4.

10. The method according to claim 9 wherein the detection threshold is in the range of 1 to 2.5.

11. The method according to claim 1 wherein the detection threshold is set to a level which is not triggered by light winds which are deemed unobtrusive.

12. The method according to claim 1 wherein the extent to which the first number and second number differ from the third number and fourth number is used to estimate a wind strength.

13. The method according to claim 1 wherein the step of determining whether the number samples in the first set differ from the number of samples in the second set to an extent which exceeds a predefined detection threshold is performed by one of McNemar's test and Stuart-Maxwell test.

14. The method according to claim 1, wherein longer block lengths are taken for higher sampling rates so that a single block covers a similar time frame.

15. The method according to claim 1 further comprising obtaining from a third microphone a respective set of signal samples.

16. The method according to claim 15 wherein a Chi-squared test is applied to the three microphone signal sample sets by use of an appropriate 3×2 observation matrix and expected value matrix.

17. The method according to claim 1 wherein a count within each sample set from each microphone is performed, and wherein for each sample set at least one of the following is counted:

number of the samples that are positive,
number of the samples that are negative,
number of the samples that exceed a threshold, and
number of the samples that are less than the threshold.

18. The method according to claim 1 further comprising determining whether the first number and second number differ from the fourth number and third number, and outputting an indication that wind noise is present only if this difference also exceeds the predefined detection threshold.

19. A device for processing digitized microphone signal to detect wind noise, the device comprising:

a first microphone and a second microphone;

a digital signal processor for:

obtaining from the first microphone a first set of signal samples;

obtaining from the second microphone a second set of signal samples arising substantially contemporaneously with the first set;

determining a first number of samples in the first set which are greater than a first predefined comparison threshold, and determine a second number of samples in the first set which are less than the first predefined comparison threshold;

determining a third number of samples in the second set which are greater than a second predefined comparison threshold, and determine a fourth number of samples in the second set which are less than the second predefined comparison threshold; and determining whether the first number and second number differ from the third number and fourth number to an extent which exceeds a predefined detection threshold, and if so output an indication that wind noise is present.

20. The device according to claim 19 wherein the device is one of: a cochlear implant BTE unit, a hearing aid, a telephony headset or handset, a camera, a video camera, or a tablet computer.

21. A non-transitory computer program stored in a storage medium and comprising computer program code to cause a computer to execute a process for processing digitized microphone signal data to detect wind noise, the process comprising:

obtaining from a first microphone a first set of signal samples;

obtaining from a second microphone a second set of signal samples arising substantially contemporaneously with the first set;

determining a first number of samples in the first set which are greater than a first predefined comparison threshold, and determining a second number of samples in the first set which are less than the first predefined comparison threshold;

determining a third number of samples in the second set which are greater than a second predefined comparison threshold, and determining a fourth number of samples in the second set which are less than the second predefined comparison threshold; and determining whether the first number and second number differ from the third number and fourth number to an extent which exceeds a predefined detection threshold, and if so outputting an indication that wind noise is present.

22. The device according to claim 19, wherein the digital signal processor applies a Chi-squared test to determine whether the number of samples in the first set differ from the number of samples in the second set to an extent which exceeds the predefined detection threshold.

23. The device according to claim 22, wherein the digital signal processor outputs an indication of an absence of wind noise when the Chi-squared test returns a value below the predefined detection threshold, and outputs an indication of the presence of wind noise when the Chi-squared test returns a value greater than the predefined detection threshold.

24. The device according to claim 19, wherein the digital signal processor estimates a wind strength based on the extent to which the first number and second number differ from the third number and fourth number.

25. The device according to claim 19, wherein the digital signal processor outputs an indication that wind noise is present only when the first number and second number differ from the fourth number and third number by a difference which also exceeds the predefined detection threshold.

* * * * *